(12) United States Patent
Bolikal et al.

(10) Patent No.: US 12,329,876 B2
(45) Date of Patent: Jun. 17, 2025

(54) POROUS BIORESORBABLE RADIOPAQUE EMBOLIC MICROSPHERES FOR DRUG DELIVERY

(71) Applicant: REVA Medical, LLC, San Diego, CA (US)

(72) Inventors: Durgadas Bolikal, San Diego, CA (US); Lioubov Kabalnova, San Diego, CA (US); Ruth Sosa, San Diego, CA (US); Ernest G. Baluca, San Diego, CA (US); Jessica Earley, San Diego, CA (US); Joann Yao, San Diego, CA (US); Elizabeth Nesseler, San Diego, CA (US)

(73) Assignee: REVA Medical, LLC, San Diego, CA (US)

( * ) Notice: Subject to any disclaimer, the term of this patent is extended or adjusted under 35 U.S.C. 154(b) by 369 days.

(21) Appl. No.: 17/272,607

(22) PCT Filed: Sep. 18, 2019

(86) PCT No.: PCT/US2019/051753
§ 371 (c)(1),
(2) Date: Mar. 1, 2021

(87) PCT Pub. No.: WO2020/061207
PCT Pub. Date: Mar. 26, 2020

(65) Prior Publication Data
US 2022/0001073 A1 Jan. 6, 2022

Related U.S. Application Data

(60) Provisional application No. 62/734,067, filed on Sep. 20, 2018, provisional application No. 62/767,293, filed on Nov. 14, 2018.

(51) Int. Cl.
*A61K 31/337* (2006.01)
*A61K 31/704* (2006.01)
*A61L 24/00* (2006.01)
*A61L 24/06* (2006.01)

(52) U.S. Cl.
CPC .......... *A61L 24/001* (2013.01); *A61K 31/337* (2013.01); *A61K 31/704* (2013.01); *A61L 24/0015* (2013.01); *A61L 24/0036* (2013.01); *A61L 24/06* (2013.01); *A61L 2300/216* (2013.01); *A61L 2300/232* (2013.01); *A61L 2300/62* (2013.01); *A61L 2430/36* (2013.01)

(58) Field of Classification Search
None
See application file for complete search history.

(56) References Cited

U.S. PATENT DOCUMENTS

| | | | |
|---|---|---|---|
| 6,284,862 B1 | 9/2001 | Kohn et al. | |
| 6,475,477 B1 | 11/2002 | Kohn et al. | |
| 7,473,417 B2 | 1/2009 | Zeltinger et al. | |
| 8,008,528 B2 | 8/2011 | Kohn et al. | |
| 8,252,887 B2 | 8/2012 | Bolikal et al. | |
| 8,415,449 B2 | 4/2013 | Kohn et al. | |
| 8,461,289 B2 | 6/2013 | Kohn et al. | |
| 8,551,511 B2 | 10/2013 | Brandom et al. | |
| 8,685,367 B2 | 4/2014 | Brandom et al. | |
| 8,765,161 B2 | 7/2014 | Kohn et al. | |
| 8,883,861 B2 | 11/2014 | Kohn et al. | |
| 9,080,015 B2 | 7/2015 | Kohn et al. | |
| 9,416,090 B2 | 8/2016 | Kohn et al. | |
| 9,605,112 B2 | 3/2017 | Kohn et al. | |
| 2006/0222681 A1* | 10/2006 | Richard | A61L 27/58 424/426 |
| 2013/0203713 A1 | 8/2013 | Kohn et al. | |
| 2015/0045451 A1 | 2/2015 | Bolikal et al. | |
| 2016/0177028 A1 | 6/2016 | Bolikal et al. | |
| 2016/0228556 A1 | 8/2016 | Hohn et al. | |

FOREIGN PATENT DOCUMENTS

| | | | |
|---|---|---|---|
| JP | 2016-529055 | 9/2016 | |
| WO | WO-2005030268 A1 * | 4/2005 | .......... A61K 31/785 |
| WO | WO 2008/138974 A2 | 11/2008 | |
| WO | WO 2013/116804 A2 | 8/2013 | |

(Continued)

OTHER PUBLICATIONS

Woodard et al (Hydrolytic Degradation and Erosion of Polyester Biomaterials. ACS Macro Lett. Aug. 21, 2018; 7(8): 976-982) (Year: 2018).*
Ulery et al (Biomedical Applications of Biodegradable Polymers. Journal of Polymer Science Part B: Polymer Physics. 2011, 49, 832-864) (Year: 2011).*
Kim et al (Polyoxalate Nanoparticles as a Biodegradable and Biocompatible Drug Delivery Vehicle. Biomacromolecules 2010, 11, 555-560). (Year: 2010).*

(Continued)

*Primary Examiner* — Jake M Vu
(74) *Attorney, Agent, or Firm* — Knobbe, Martens, Olson & Bear, LLP

(57) ABSTRACT

Methods, copolymer materials and devices are provided for embolic arterial interventions (embolization therapy or embolotherapy). More particularly, radiopaque, bioresorbable spherical microparticles for embolization or vascular occlusion therapies, comprising copolymers of iodine-containing, halogenated phenyl-containing units, such as iodinated desaminotyrosine derivatives, and rubbery components, such as polyethylene glycol (PEG), polycaprolactone (PCL), polytetramethylene oxide (PTMO) or polytrimethylene carbonate (PTMC), are provided. The provided microbeads may further contain, or be coated with, therapeutic agents such as paclitaxel, for targeted delivery of the therapeutics.

17 Claims, 9 Drawing Sheets

(56) References Cited

FOREIGN PATENT DOCUMENTS

WO     WO 2016/103224 A2     6/2016
WO     WO 2017/111994 A1     6/2017

OTHER PUBLICATIONS

Murthy, N.S. et al., "Microphase separation in copolymers of hydrophilic PEG blocks and hydrophobic tyrosine-derived segments using simultaneous SAXS/WAXS/DSC", Polymer (2010), vol. 51 Issue 17, pp. 3978-3988.

Regazzoli, D. et al., "New generation bioresorbable scaffold technologies: an update on novel devices and clinical results", Journal of Thoracic Disease (2017), vol. 9 Supplement 9.

* cited by examiner

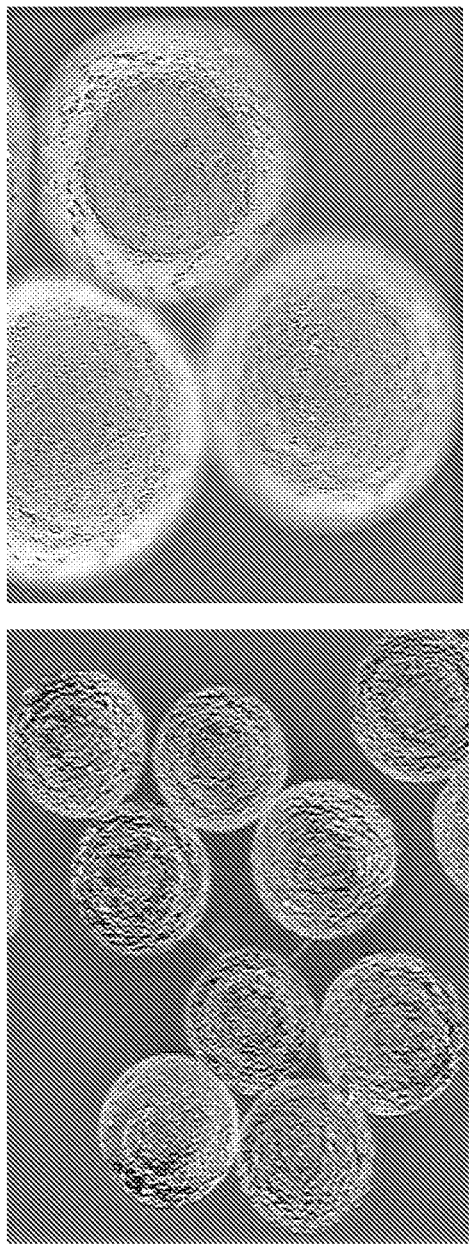
FIG. 9A
FIG. 9B
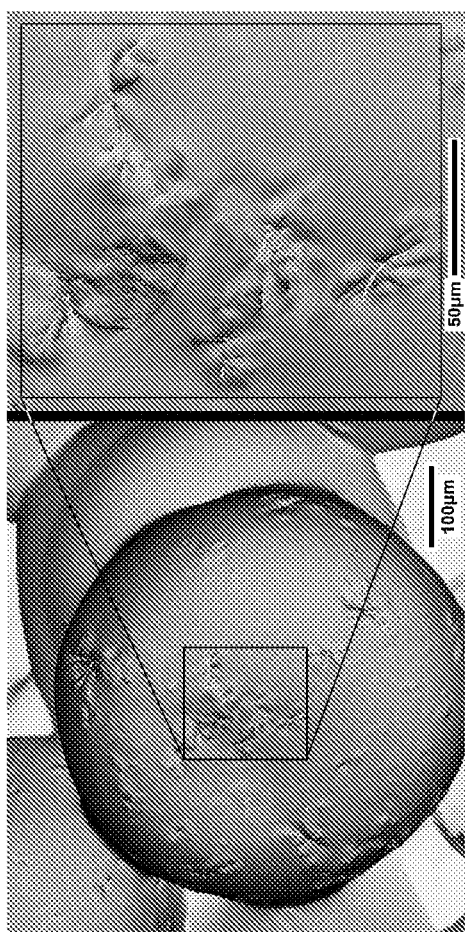
FIG. 10

POROUS BIORESORBABLE RADIOPAQUE EMBOLIC MICROSPHERES FOR DRUG DELIVERY

INCORPORATION BY REFERENCE TO ANY PRIORITY APPLICATIONS

The present application claims the benefit of priority to U.S. Provisional Application Nos. 62/734,067, filed Aug. 20, 2018, and U.S. Pat. No. 62,767,293, filed Nov. 14, 2018, which are hereby incorporated by reference in their entireties.

BACKGROUND

Field

Embodiments of the present disclosure relate to methods, materials and devices for embolic arterial-interventions generally, and more particularly to methods and devices for time-controlled embolic occlusion of blood circulation in target tissues by means of radiopaque, bioresorbable microspheres.

Embolotherapy devices and reagents include metal embolic coils, plugs, gel foams, polymeric glues, sponges, detachable balloons, oils, alcohol, and particulate polymeric embolic agents. These may be used, for example, to control bleeding, prevent blood loss prior to or during a surgical procedure, restrict or block blood supply to tumor, vascular malformations or other tissue site.

Over the past decade, substantial improvements were made in the development of therapeutic embolotherapy, and in particular in the use of spherical microparticles or beads.

Particulate embolic agents such as microspheres may be used, for example, in minimally invasive procedures to restrict or block blood supply in applications in which typically the embolic particles are delivered, under X-ray guidance, through a guide catheter inserted into the vasculature, so as to guide deployment to a target site, which may be a tumor or a vascular malformation. Examples include uterine fibroids, cancerous tumors (i.e., hepatocellular carcinoma or HCC), hemorrhage (e.g., during trauma with bleeding) and arteriovenous malformations (AVM), fistulas and aneurysms, and the like. The particles used for clinical applications are typically suspended in a radiopaque contrast solution and delivered through a vascular catheter via syringe injection.

Spherical microparticles (the terms spherical microparticles, spherical microbeads, and simply microbeads, are generally used interchangeably herein) are often favored for tumor embolization because spherical particles can provide more precise and uniform sizing, better positioning control, and ability of distal microcatheter delivery for deeper penetration into vasculature. Spherical microparticles minimize such disadvantages of other embolization devices as perforation of blood vessels, shrinkage of embolic material, fragmentation and downstream release of particles from sponges, gels and glues.

Transcatheter arterial chemoembolization or TACE is a procedure whereby embolic particles or beads carry chemotherapeutic drugs which are released following application of the particles to restrict the blood supply to a target tissue, such as a tumor. Thus, the particles may both block the blood supply and induce cytotoxicity to attack a tumor.

Radiopaque embolic beads have the potential distinct advantage of being visible under X-rays during and after embolic therapy procedures. During the procedure, visualization of the particulate agent can allow the physician to affect precise delivery to the targeted vessel or tissue, and to ensure that the particles do not become resident in unintended sites. Once the radiopaque particles have been implanted, follow-up procedures could be limited to non-interventional methods, e.g., simple X-Ray radiography. In the case of a tumor, for example, its size could be tracked since the radiopaque embolized sections would be shown converge as the mass/volume decreased with time.

Bioresorbable embolic particles, beads or microspheres have the potential advantage of being temporary. The effective removal of the particulate foreign body over time allows the surrounding tissue to return to its unaffected state. Bioresorbable embolic particles also allow for retreatment at the site of initial embolization and help minimize collateral revascularization.

A number of spherical embolic particles have been developed for different transcatheter arterial embolization indications. Currently, different types of embolic microspherical products are available on the market including Embosphere™ and HepaSphere/QuadraSphere™ from Merit Medical; Bead Block™, LC Bead™, LC Bead LUMI™, DC Bead™ and DC Bead LUMI™ from BTG International; Contour SE™ and Embozene™ from Boston Scientific Corp.; HydroPearl™ and LifePearl™ from Terumo Corp, among others.

Spherical microbeads have been developed in varieties of sizes (1-1200 μm), internal structures (solid, porous, capsular) and surface morphologies (smooth or rough, intentionally enlarged surface). For example, U.S. Pat. No. 8,617,132 (Golzarian, et al.) describes embolic microspheres comprising carboxymethyl chitosan crosslinked with carboxymethyl cellulose. The range of functionalities of the commercially available microbeads also include biodegrability [1, 2, 3], drug loading and drug elution capability [4,5], and X-ray visibility [6-8], but not all in the same product.

However, there remain limitations in the functionality available in any single embolic microbead or microsphere, placing limits on applications. Currently, there are no beads combining radiopacity, degradability, properties for deliverability, and drug delivery; in one microbead.

SUMMARY

There are multiple parameters of microbeads that have a significant influence on their functional behavior. Many of these parameters are interrelated with one another and defined primarily by composition of polymer material. Among those the most significant parameters are radiopacity, biodegradability, ease of physical handling, buoyancy, optimized mechanical behavior (compressibility and resilience), fluid dynamics, and occlusive behavior.

As set forth herein, embodiments of the present disclosure address these needs, and which provide spherical microbeads combining radiopacity, degradability, ability to deliver pharmaceutical and/or biologic agents and properties for deliverability; in one microbead.

Also as set forth herein, embodiments of the present disclosure include microbeads comprising porous polymeric materials. Embodiments include generally spherical microbeads which comprise inherently radiopaque bioresorbable polymer materials which are porous.

Also as set forth herein, embodiments of the present disclosure include microbeads comprising a content of a therapeutic drug or other agent. Embodiments include both porous microbeads and non-porous microbeads which comprise a content of a therapeutic drug or other agent.

Some embodiments of the present disclosure relate to embolic spherical microparticles, comprising: a copolymer material having at least one radiopaque iodine-containing component and at least one rubbery component; wherein the rubbery component comprises a polymer material having a Tg below a physiological temperature of about 37° C., the rubbery component comprising oligomeric PEG, PCL, PTMO, PTMC or combinations thereof; and wherein the radiopaque component comprises halogenated phenyl-containing monomer or oligomer units. In some embodiments, the microparticles have internal and/or external porosity. In some further embodiments, the microparticles are radiopaque and biodegradable.

In some embodiments of the embolic spherical microparticles described herein, the copolymer material comprises monomer or oligomer units connected by two or more different chemical bonds with different affinities to hydrolysis such that the different chemical bonds have different rates of in vivo hydrolytic degradation. In some such embodiment, the rate of hydrolytic degradation of the copolymer material is controlled by the relative amount of faster and slower degrading chemical bonds. In some such embodiments, the ratio of fast to slow degrading chemical bonds is in the range from about 100:1 to about 1:100, from about 5:95 to about 95:5, from about 10:90 to about 90:10, from about 20:80 to about 80:20, from about 30:70 to about 70:30, from about 40:60 to about 60:40, or about 50:50. In some such embodiments, the in vivo dissolution or degradation of the microparticles is in the range from one minute to a few years.

In some embodiments of the embolic spherical microparticles described herein, the ratio of radiopaque iodine-containing component to the rubbery component is from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, from about 2:1 to about 1:2, or about 1:1.

In some embodiments, the copolymer comprises more than one rubbery components with different hydrophilicity and different affinity to swelling in water or biologically relevant liquid media, and wherein the ratio between two different rubbery components with different hydrophilicity/swelling ability is in the range from about 100:1 to about 1:100, from about 5:95 to about 95:5, from about 10:90 to about 90:10, from about 20:80 to about 80:20, from about 30:70 to about 70:30, from about 40:60 to about 60:40, or about 50:50. In some such embodiments, the hydration of the microparticles to about 80%-90% of a fully hydrated state may occur in 1 to 3 minutes following contact with a liquid aqueous media. In some embodiments, wherein the copolymer comprises more than one rubbery components with different hydrolytic degradation rates, and wherein the ratio between fast and slow degrading rubbery components is in the range of from about 100:1 to 1:100, from about 5:95 to about 95:5, from about 10:90 to about 90:10, from about 20:80 to about 80:20, from about 30:70 to about 70:30, from about 40:60 to about 60:40, or about 50:50.

In some embodiments of the embolic spherical microparticles described herein, the microparticles have internal and/or external porosity. In some such embodiments, the porosity is created after microparticle formation due to the decomposition of fast-degrading chemical bonds and the release of volatile(s) or gas(es) resulted from the decomposition. In some further embodiments, the volatile(s) or gas(es) form pores and/or "escape" channels. In one embodiment, the volatile or gas is carbon dioxide. In some other embodiments, the porosity is created by incorporation of one or more porogen materials during microparticle formation and subsequent elimination of the porogens from the formed microparticles.

In some embodiments of the embolic spherical microparticles described herein, the microparticles are highly compressible. In some embodiments, the microparticles are highly resilient. In some such embodiments, the microparticles are capable of returning to the original shape and size, or return to about 90%-100% of the original diameter or size. In some such embodiments, the original state may refer to the "dry" state of the microparticles before contact with a liquid or aqueous environment. In some other embodiments, the original state refer to the "hydrated" state of the microparticles after contact with a liquid or aqueous environment.

In some embodiments of the embolic spherical microparticles described herein, the rubbery component of copolymer material comprises oligomers or macromers of one or more of PEG, PCL, PTMO, PTMC or combinations thereof.

In some embodiments, the radiopaque iodine-containing component comprises monomers, oligomers and/or macromers of one or more of I2DTE, I2DAT; PrD-di I2DAT or combinations thereof. In some further embodiments, the radiopaque iodine-containing component comprises a repeating unit having the structure:

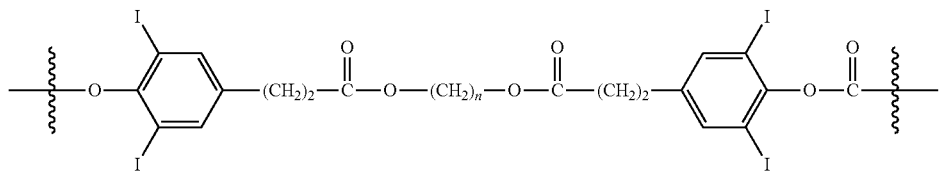

wherein n is an integer from 1 to 18. In one embodiment, the radiopaque iodine-containing component comprises PrD-di I2DAT.

In some embodiments, the microparticles comprise a blend of at least two different constituent copolymers, each of the constituent copolymers comprises a main polymer chain having an amount of carbonate bonds and an amount of oxalate bonds; and wherein the two constituent copolymers differ substantially in the amount of oxalate bonds relative to the amount of carbonate bonds such that one of the two constituent copolymers hydrolytically degrades in vivo at a higher rate than the other constituent copolymer, resulting in a multiple step or phased degradation of the microparticles.

In some embodiments, the microparticle further comprises one or more therapeutic agents. In some such embodiments, the microparticles are configured to deliver and achieve controlled release of the one or more therapeutic agents. In some further embodiments, the one or more therapeutic agents is selected from the group consisting of Cisplatin, Doxorubicin, Cyclophosphamide, Paclitaxel, Oxaliplatin, 5-Flourorcil, Nivolumab/Pembrolizumab, Ipilimumab, Interleukin-2, and combination and analogs thereof. In some further embodiments, the therapeutic agent is diffused into the pores of the microparticles. In other embodiments, the therapeutic agent is encapsulated in the microparticles. In further embodiments, the microparticles are prepared by precipitated from a solution comprising the copolymer material and the therapeutic agent.

Additional embodiments of the present disclosure relate to an embolization suspension, comprising a solution or solvent, and the embolic spherical microparticles described herein suspended in the solution or solvent, wherein the microparticles are hydrated and have diameters between about 40 μm to about 2000 μm, between about 50 μm to about 1500 μm, between about 60 μm to about 1000 μm, between about 70 μm to about 900 μm, between about 80 μm to about 800 μm, between about 90 μm to about 700 μm, or between about 100 μm to about 600 μm. In some embodiments, the suspension further comprises a contrast medium and a saline solution. In some such embodiments, the contrast medium and the saline solution are in the ratio from about 10:90 to about 90:10, from about 20:80 to about 80:20, from about 30:70 to about 70:30, from about 40:60 to about 60:40, or about 50:50.

Further embodiments of the present disclosure relate to a method of preparing a copolymer material for inclusion in embolic microparticles, comprising: performing condensation polymerization of at least two different pre-polymer components; wherein the condensation polymerization is achieved by addition of at least two different coupling agents; and wherein the addition of the at least two different coupling agents results in the formation of chemical bonds having different affinity to hydrolysis and/or thermal degradation along copolymer chains of the copolymer material. In some embodiments, the addition of at least two different coupling agents occurs in a simultaneous manner. In such embodiments, the condensation polymerization results in the formation of relatively even distribution of faster and slower hydrolysable chemical bonds along the copolymer chains. In other embodiments, the addition of the at least two different coupling agents occurs in a consecutive or sequential manner. In such embodiments, the condensation polymerization results in the formation of blocks with faster hydrolysable chemical bonds, and blocks with slower hydrolysable chemical bonds along the copolymer chains. In other embodiments, the addition of the at least two different couple agents comprises alternating addition of the different coupling agents in a plurality of sub-portions. In such embodiments, the condensation polymerization results in the formation of relatively small blocks of faster and slower hydrolysable chemical bonds along the copolymer chains. In some embodiments, the different coupling agents comprises at least one of oxalyl chloride and triphosgene (TP).

Further embodiments of the present disclosure relate to a method of preparing porous spherical microbeads, comprising: providing a polymer material prepared according to the method described herein; dissolving the polymer material in an appropriate solvent; and streaming the polymer containing solvent into a receiving solution to form microbeads; wherein volatile gases are generated by simultaneous partial decomposition of highly hydrolysable chemical bonds within the polymer material, resulting in the formation of interior pores within the microbeads. In some embodiments, volatile gases escaping from the microbeads creates open and/or exterior surface porosity. In some embodiments, the formation of the microbeads from the copolymer solution happens simultaneously with partial decomposition of thermally unstable chemical bonds in the microbeads, thus creating porosity inside and/or outside the microbeads.

Further embodiments relates to a method of forming spherical cross-linked microbeads, comprising: incorporating (hydroxyethyl)methacrylate (HEMA) in a polymer composition; adding a free radical initiator to a solution of polymer; forming microbeads from the polymer solution, such that the free radical initiator diffuses into the microbeads; and initiating polymer cross-linking. In some embodiments, the polymer cross-linking is initiated by applying heat.

Further embodiments relate to embolic spherical microparticles comprising a blend of at least two different constituent copolymers, wherein either or both of two constituent copolymers are prepared according to the method described herein, wherein the coupling agents are selected such that the two constituent copolymers differ substantially in the relative content of the chemical bonds produced by the two different coupling agents; such that one of the two constituent copolymers hydrolytically degrades in vivo at a higher rate than the other constituent copolymer, resulting in a multiple step or phased degradation. In some embodiments, the microparticles further comprises at least one therapeutic agent, the microparticles are configured to release the therapeutic agent during in vivo degradation of the copolymers, and wherein the release is substantially coordinated with the multiple step or phased degradation.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments.

FIGS. 9A-9B illustrates copolymer microbeads prepared from copolymer 50% PrDI2FD-co-30% PEG1 k-20% PCL1.25 k with ratio of carbonate to oxalate bonds=75% to 25%, diffused with Doxorubicin. FIG. 9A: before incorporation drug Doxorubicin (DOX); and FIG. 9B: fully DOX-loaded microbeads.

FIG. 10 shows a microbead made by precipitation of crystalline Paclitaxel as a mixture in a copolymer material.

DETAILED DESCRIPTION

Figure 1:
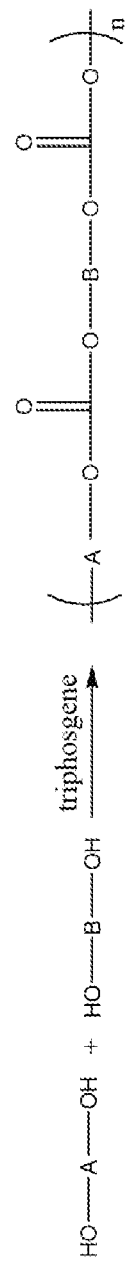
FIG. 1 illustrates a generalized reaction scheme for condensation polymerization with triphosgene (TP) of two monomers A and B (e.g., PrD-diI2DAT and PEG).

According to aspects of the present disclosure, certain embodiments comprise embolic spherical radiopaque microparticles comprised of a copolymer material synthesized from at least one radiopaque iodine-containing component and at least one rubbery component, the combination of these in the resulting polymer providing a desirable combination of properties.

The radiopaque component may comprise halogenated phenyl-containing monomer or oligomer units, such as those described herein above. Preferably, the halogen content is all or chiefly iodine. According to aspects of the present disclosure, certain embodiments comprise copolymers including units of a di-ester of 1, 3-propanediol with di-iodinated-desaminotyrosine. Alternative embodiments include di-ester of other diols with di-iodinated-desaminotyrosine, for example, ethylene glycol, butyl diol, alkyl diols generally, oligomers of polyethylene glycol (PEG), and the like.

The rubbery component may comprise a polymer material which has a Tg (glass transition temperature) below a physiological temperature of about 37° C., to provide flexibility and resilience during and after implantation in the vasculature. For example, the rubbery component of the copolymer material may comprise oligomeric units of PEG, polycaprolactone (PCL), poly(tetramethylene oxide) (PTMO), poly(trimethylene carbonate) (PTMC) or combinations of thereof. More than one rubbery component can be used to adjust such properties of copolymer as biodegradation, "stickiness", resilience, etc.

Definition

The section headings used herein are for organizational purposes only and are not to be construed as limiting the subject matter described.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Radiopacity

Radiopacity of embodiments of microbeads is provided by incorporation of one or more kinds of halogen-containing monomers. Radiopacity of the microbeads can be adjusted by varying the amount of the radiopaque components in copolymer. As noted above, the radiopacity of the microbeads of the present disclosure allows precise positioning of the beads at the target location and allows to determine the "end point" of embolization.

The radiopaque constituent may comprise a monomer or macromer which includes halogen-substituted phenyl rings, which serve as a radiopaque entity when incorporated into the polymer structure of the microsphere or bead. Typically, such halogen-substituted phenyl rings contribute to the rigidity of copolymer materials and may be referred to herein as a "rigid" component.

In preferred embodiments, the halogen is iodine. A number of suitable halogenated phenolic constituents are described in the following US patents and US published patent applications: U.S. Pat. Nos. 6,284,862; 6,475,477; 8,685,367; 7,473,417; 8,008,528; 8,461,289; 8,551,511; 8,252,887; 8,415,449; 9,080,015; 8,765,161; 9,605,112; 8,883,861; 9,416,090; 2015-0045,451; and 2016-0177,028.

For example, U.S. Pat. No. 9,416,090 (among others) describes monomers and polymers in which comprise desaminotyrosyl tyrosine ethyl ester, generally abbreviated as DTE. The DTE may be halogen-substituted at various positions and to varying degrees. Examples of variants of di-iodinated DTE are shown below, often abbreviated as I2DTE, (there are several possible variants for iodine substitution, e.g. 1-4 substitutions at different locations, see U.S. Pat. No. 9,416,090):

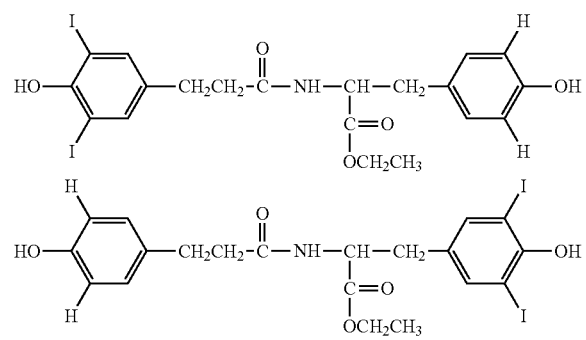

In another example, U.S. Pat. No. 8,252,887 describes a monomer which comprises two units of di-iodinated desaminotyrosine (generally abbreviated I$_2$DAT) linked by ester bonds to a alkyl linking unit (CH$_2$)$_n$, wherein n is an integer from 1 to 18.

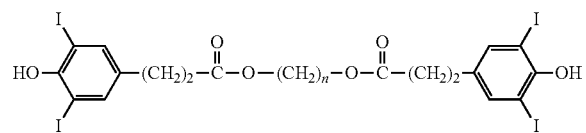

In a preferred embodiment, n=3 and the linking unit is 1,3 propane diol, such that the monomer is a di-ester of 1,3-propanediol ("PrD") with I$_2$DAT. This compound (and related polymeric forms) may be referred to herein as "PrD-di I2DAT".

Copolymer Elastomeric Constituent

Certain microbead embodiments having aspects of the present disclosure include copolymers comprised of at least two different biodegradable components—radiopaque constituent based on halogen-containing monomers and an elastomeric constituent with glass transition temperature below physiological temperature (below about 37° C.). This component may be referred to also as a "rubbery component", "soft component", or the like.

An elastomeric constituent may comprise one or more monomer or oligomer species. For example, in certain embodiments, the elastomeric phase may comprise, among other things, units of polyethylene glycol (PEG).

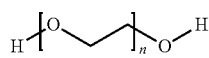

The molecular weight (MW) of a PEG unit depends on the value of "n", which may be selected to suit desired properties. For example, an elastic component may include PEG repeating units having a range of molecular weight, characterized by an average value and range of "n". Oligomers of PEG are commercially available in several size or MW ranges. See, for example, Sigma-Aldrich (now Millipore Sigma) markets PEG materials or solutions with molecular weights from about 200 to about 50,000 g/mol.

Other materials may be employed instead of or in combination with PEG for inclusion in the elastomeric component, such as oligomeric polycaprolactone (PCL), poly(tetramethylene oxide) (PTMO), poly(trimethylene carbonate) (PTMC) or combinations of thereof.

Materials Incorporating Fast-Degrading Chemical Bonds

In some instances, embodiments described herein include chemical bonds having different affinity to hydrolysis and/or thermal degradation in linkages along copolymer chains of the copolymer material, and that such differences may effect several distinct properties of the embodiments of the copolymer materials of the present disclosure.

In certain embodiments, the effects of such fast-degrading bonds can be complementary, and useful to a medical product, such as an embolic microsphere or microbead. In some embodiments, such fast-degrading bonds may be included along with other relatively stable linkage bonds to connect monomers or oligomer constituents of the copolymer material (e.g., linking a radiopaque component and/or an elastomeric constituent).

In exemplary embodiments described below, the fast-degrading bond may be an oxalyl ester bond, and may be incorporated in conjunction with carbonate bonds, which are relatively stable in comparison under conditions of hydrolysis and/or thermal degradation. In certain embodiments for making copolymer materials, agents such as triphosgene (TP) and oxalyl chloride may be employed as reactant in creating linkages in a copolymer chain.

In one embodiment of a copolymer composition having a mixture of carbonate and oxalate bonds may be employed as a constituent in making an embodiment of microbead herein, whereby the portion of Oxalate bonds may be selected so as to tailor both the in vivo degradation characteristics of the microbead, and induce a desired porosity during the formation of the microbeads.

Additionally a polymer containing the fast-degrading bond may be blended with a polymer with the more stable carbonate bonds in making an embodiment of microbead herein, whereby the portion of Oxalate bonds may be selected so as to tailor both the in-vivo degradation characteristics of the microbead, and induce a desired porosity during the formation of the microbeads.

Tunable Degradation Rate Due to Polymerization Bond Types

Degradation of microbeads embodiments of the present disclosure can be tuned from hours to months, or even years depending mostly on the amount of incorporated fast degrading chemical bonds. In certain embodiments, the monomeric units of copolymer are connected by at least two different types of chemical bonds with different degree of susceptibility to hydrolysis and thermal degradation.

In some embodiments, the comprising monomeric units of copolymer are connected by relatively slow-degrading carbonate bonds created by condensation reaction with phosgene as a coupling agent.

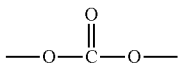

This resulting carbonate bond in the copolymer chain has a relatively low reactivity to hydrolysis under physiological conditions (e.g., in vivo). For example, FIG. 1 illustrates a reaction scheme for an example of a carbonate copolymer made using triphosgene (TP) as a reactant (see, e.g., EXAMPLE 1).

In some embodiments, the comprising monomeric units are connected by oxalyl ester chemical bonds created by polycondensation reaction with oxalyl chloride as a coupling agent reactant (see, e.g., EXAMPLE 2).

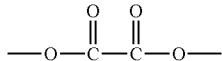

Figure 2:
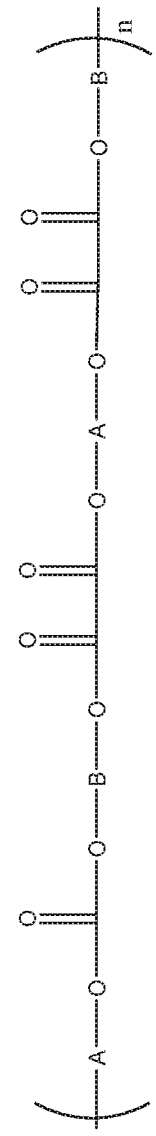
FIG. 2 illustrates the chemical structure of an exemplary generalized copolymer with mixture of carbonate and oxalate bonds.

The oxalyl ester bonds are more prone to hydrolysis under physiological conditions (e.g., in vivo) than are the carbonate bonds, so as to accelerate biodegradation of the copolymer chain. For example, FIG. 2 shows a generalized copolymer having a mixture of Oxalyl and Carbonate bonds.

Because of polycondensation nature of polymerization reaction, addition of more than one coupling agent may be varied in different manners (e.g., by simultaneous, sequential, and/or alternating addition), leading to incorporation of different chemical bonds in the same copolymer macromolecule, which are described in details in Examples 3-5 below.

Porosity of Microbeads.

In some embodiments, the porosity of microbeads may be tuned by compositional changes and bead-forming conditions. Microbeads may be prepared to be non-porous, or alternatively, to have substantial interior porosity. A specific preparation is described in Examples 7 and 8 below.

Similarly, microbeads may be prepared with interior porosity extending to particle surface. This property may be referred to herein as have internal external and/or internal/external porosity. See, for example, a highly porous microbead shown in FIG. 3.

In one embodiment, the interior porosity of the microbead is introduced by creating the channels by carbonate dioxide forming during decomposition prone to hydrolysis oxalyl ester chemical bonds. Alternatively, porous microbead embodiments may be also prepared by traditional method for creating porous materials such as porogen leaking method when porogen material (salt, DMSO, ice particles, etc.) is incorporated into the beads during bead formation and later removed leaving the negative replica pores.

Density of Radiopaque Materials and Buoyancy.

Introduction of a degree of porosity is especially useful for radiopaque microbeads having aspects of the present disclosure because inclusion of iodine in polymer formulation increases their density. The introduction of porosity substantially increases buoyancy of microbeads, and thus, the introducing of porosity into the microbead can be used to counter-balance the density effect of iodine. The balancing buoyancy serves to avoid rapid sedimentation, so as to improve the deliverability of microbeads.

Hydration and Swelling of Microbeads.

Figure 4:
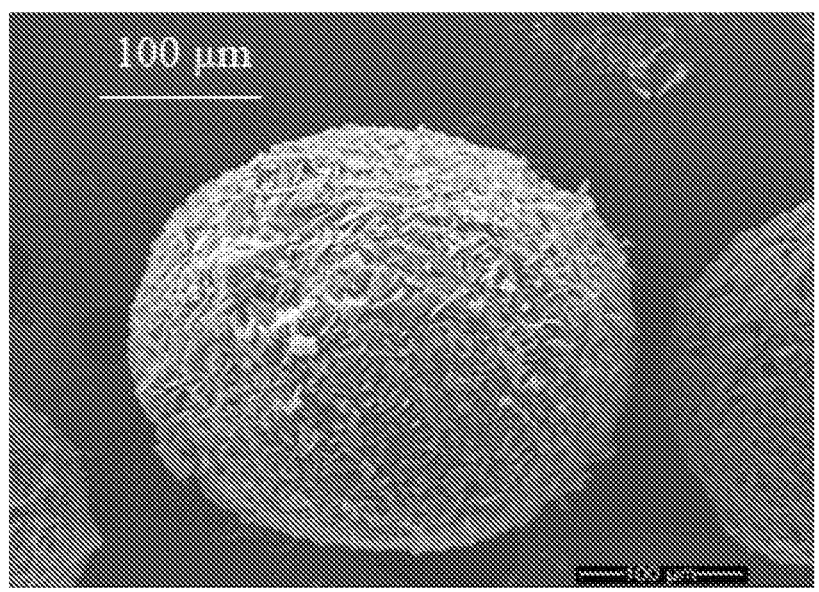
FIG. 4 is a SEM image of exemplary embodiments of spherical dry embolization microparticles covered with mannitol coating.
Figure 5A:
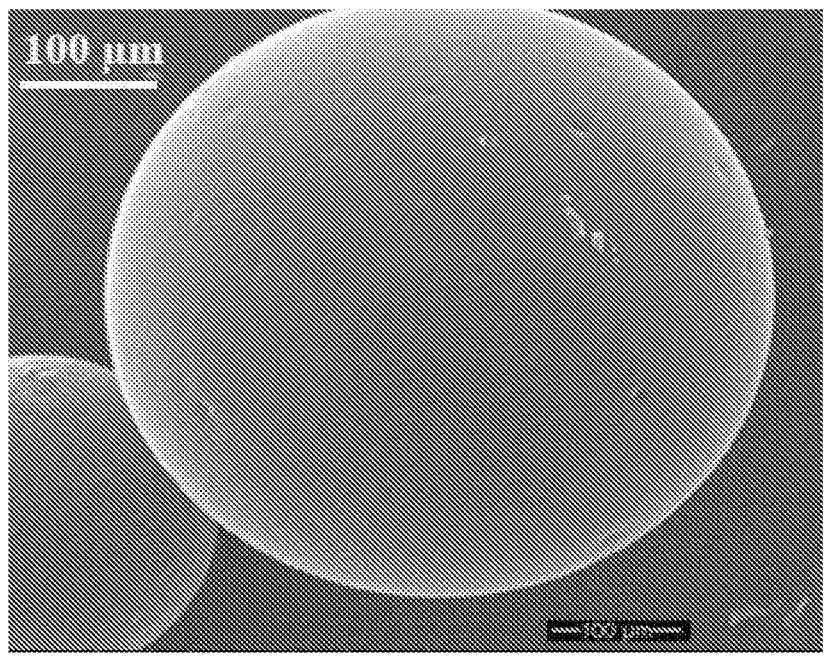
FIGS. 5A and 5B are SEM images of exemplary embodiments of spherical fully hydrated non-porous embolization microparticles at two different magnifications.
Figure 5B:
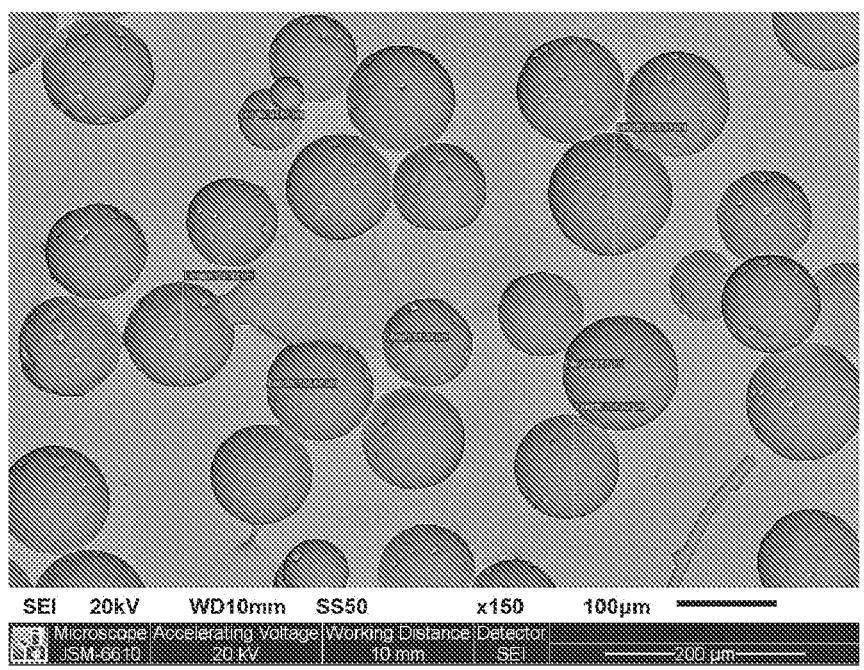
Figure 6:
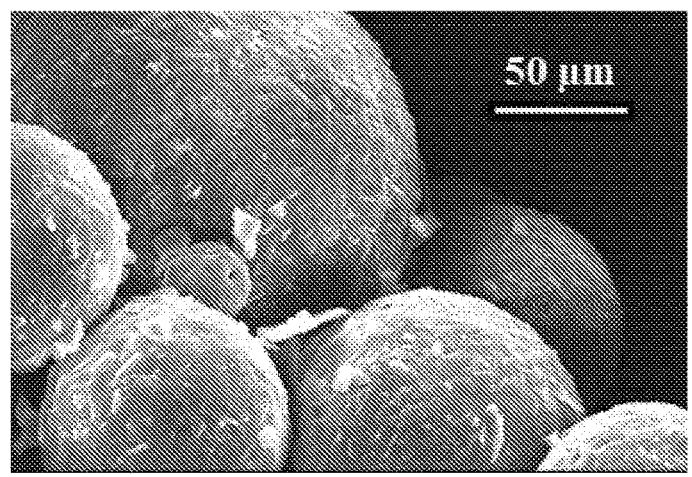
FIG. 6 is a SEM image of additional exemplary embodiments of spherical dry embolization porous microparticles (covered with mannitol coating).
Figure 7A:
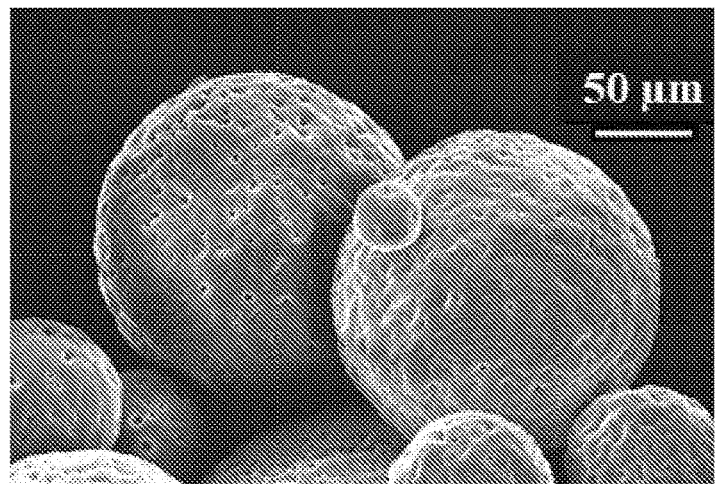
FIGS. 7A and 7B are SEM images of additional exemplary embodiments of spherical fully hydrated porous embolization microparticles at two different magnifications.
Figure 7B:
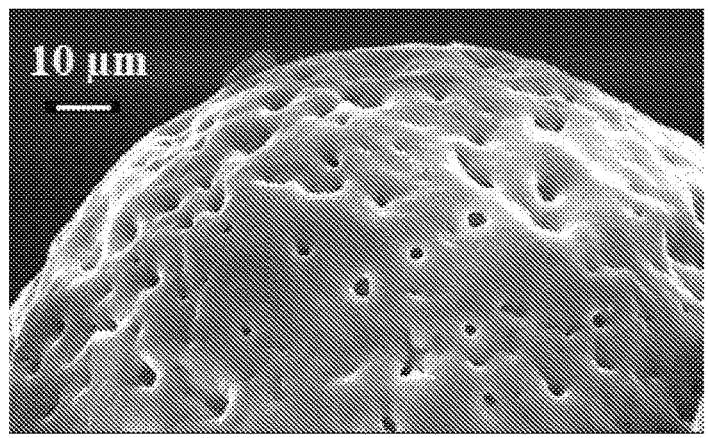

Embodiments of the microbeads of the present disclosure may be produced in a dry state, so as to postpone response to aqueous fluids. Upon contact with water, contrast or water-contrast solution, microbeads may be configured to quickly absorb water and swell. After initial fast swelling (1-3 minutes), the density of microparticles gets substantially lower than density of dry beads, especially for porous beads. For example, the exemplary microbeads shown in dry form (FIGS. 4 and 6) and hydrated form (FIGS. 5A, 5B, 7A and 7B).

Such solvated microparticles have substantially lower tendency to interact and aggregate with each other and they form a suspension in solution with a rate of sedimentation allowing the hydrated microbeads to be delivered by passing through microcatheters with appropriate lumen size. Some additional smaller swelling of microbeads occurs after placement the microbeads into an occlusion site. This additional small expansion of microbeads creates a pressure against the wall of vascular vessel, and embolization microparticles may thus conform to a cross section of the vessel.

Certain embodiments of microbeads may comprise a copolymer material including more than one rubbery component, and wherein the different rubbery components have different hydrophilicity and different affinity to swelling in water or biologically relevant liquid media. The relative amount of hydrophobic to hydrophilic components has substantial effect on swelling on the beads, their buoyancy and mechanical properties. The ratio between rubbery components with different hydrophilicity/swelling ability can be in the ratio from 100:0 to 0:100.

Size and Size Distribution

The embolic materials of the present disclosure may be formed into dry microspheres with diameter between 30 μm and about 1500 μm. Different applications require different sizes of beads, depending on the anatomy. The size of microspheres is crucial for anatomical compatibility, fluid dynamics, deliverability and level of occlusion. Microbeads of the present disclosure could be produced in narrow or broad size ranges. Smaller microspheres usually penetrate deeper into the vessels, while bigger size microspheres have bigger chance to block the vessel and prevent penetration of smaller beads. For example, FIG. 3 through FIGS. 7A-7B present images with scales of a number of embodiments of microbeads described herein.

Compressibility and Resilience

Compressibility and resilience of microbeads are crucial for delivery procedure, when microbeads are compressed during the travel through a microcatheter but should quickly recover its original size after injection from catheter.

In some embodiments, compressibility and resilience of microbeads is regulated by the amount of rubbery component in copolymer composition. In some other embodiments, compressibility and resilience of microbeads is regulated by the molecular weight of rubbery component, by the molecular weight of the synthesized copolymer material, or by the presence of porosity.

In some embodiments, the hydrated microbeads are compressible from original hydrated spherical shape to a substantially deformed elongated cylinder-like shape that can subsequently bounce back toward their original shape. This compressibility under strain feature of microbeads allows the microbeads to be compressed into delivery catheter with diameter that is smaller than the diameter of hydrated microbeads. Resilience allows microbeads to recover up to 90%-100% of original hydrated state in seconds upon exiting the catheter. In some embodiments, the microparticles are highly compressible, such that the microparticles may be compressed to about 5%, 10%, 15%, 20%, 25%, 30%, 35%, 40%, 45%, 50%, 55%, 60%, 65%, 70%, 75%, 80%, 85%, 90% or 95% of its original size or diameter prior to applying the compression force, or within a range between any of the two preceding values. In some embodiments, the microparticles are highly resilient, such that the microparticles are capable of returning to the original shape and size, or to about 50%, 55%, 60%, 65%, 70%, 75%, 80%, 85%, 90%, 95%, 99% or 100% of the original diameter following release of compression force, or a range defined by any of the two preceding values. In some further embodiments, the microparticle may return to about 90%-100% of the original diameter or size. In some such embodiments, the original state may refer to the "dry" state of the microparticles before contact with a liquid or aqueous environment. In some other embodiments, the original state refer to the "hydrated" state of the microparticles after contact with a liquid or aqueous environment. In further embodiments, the microparticles are highly resilient in the hydrated state.

Figure 8:
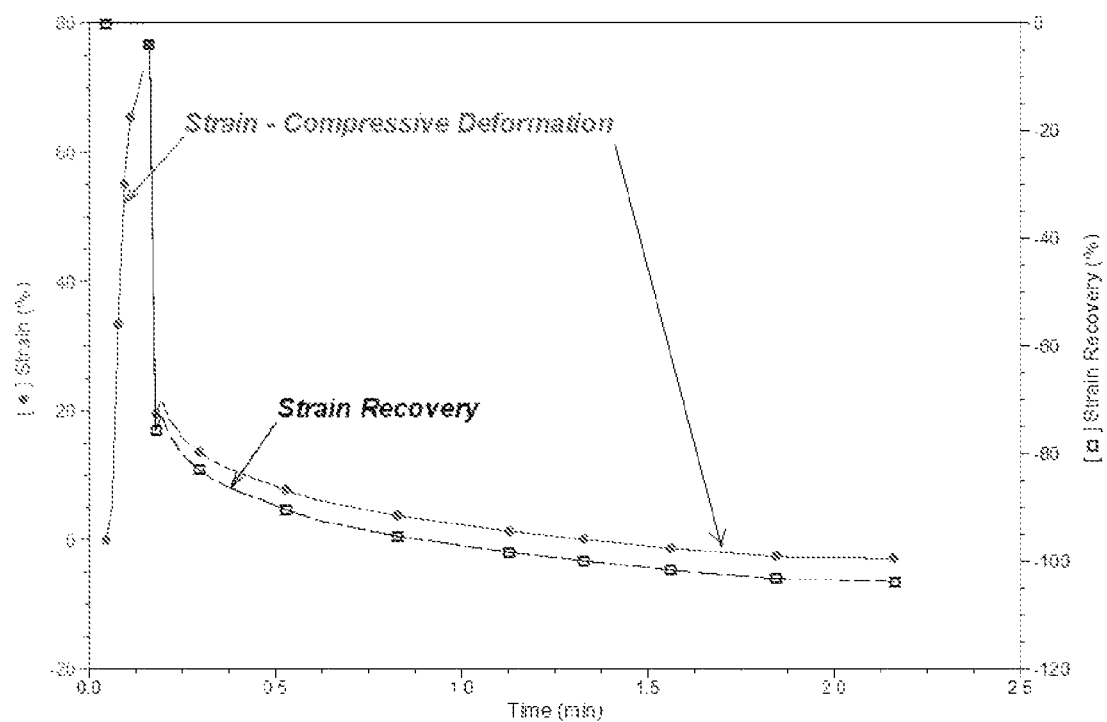
FIG. 8 illustrates the compression and size recovery of individual microbead in DMA stress-relaxation mode test.

FIG. 8 illustrates the compression of individual bead (350 µm diameter) to 80% in DMA compression test performed under water and quick strain recovery after unloading the microbead. In this example, the microbeads are formed of Poly(50% PrD-di I2DAT-co-50% PEG1K 100% carbonate).

Relative Properties of Microbeads

Generally, as the % content of the radiopaque component increases, not only does radiopacity increase, but structural rigidity and degradation time increases. This may result in a decrease in compressibility.

Generally, as the % of oxalate bonding relative to carbonate bonding increases, both porosity and buoyancy increase on the one hand; and hydrolytic degradation rate increases on the other hand.

Method of Microbeads Preparation

The present disclosure also provides a method of making spherical, radiopaque, biodegradable, compressible, resilient microparticles with interior and exterior porosity. Porosity of microparticles is created by formation of carbon dioxide gas which is formed during microbeads preparation due to degradation of previously incorporated easily hydrolysable or thermally instable chemical bonds.

In some embodiments, the porosity of microparticle could also be created by incorporation of porogen materials during beads formation stage and subsequent elimination them from already formed microbeads.

Microbead Drug Content and Drug Delivery

In some embodiments, the radiopaque, biodegradable microbeads described herein comprise at least one drug or pharmaceutic agent which may be released at the site of embolic implant. The term "drug" as used herein is not intended to be limiting and may include either or both of small-molecule compounds and large-molecule compositions or biologic agents. Thus, the term "drug" is broadly intended to include "therapeutic agents" as generally known in medical science.

Drugs and Therapeutic Agents Generally

According to one embodiment of the embolotherapy products and methods described herein, the polymers may be formulated with an effective amount of at least one therapeutic agent (e.g., a pharmaceutical agent and/or biologic agent) sufficient to exert a selected therapeutic effect.

The term "pharmaceutical agent", as used herein, encompasses a substance intended for mitigation, treatment, or prevention of disease that stimulates a specific physiologic (metabolic) response.

The term "biologic agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands.

Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)).

Further the term "biologic agent" may include:

1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules;

2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation.

The therapeutic agent may also include vitamin or mineral substances or other natural elements.

Pre-Loaded Embolic Microbeads, and "Bed-Side" Drug Loading

In some embodiments, radiopaque, bioresorbable embolic microbeads described herein are pre-loaded with a drug or therapeutic agent content, as supplied to an end user (e.g., treating physician). In some embodiments, the microbeads described herein are configured to be loaded with a drug or therapeutic agent at the time of use by application of the therapeutic agent by the end-user (e.g., a therapeutic agent infused into microbead embodiments by a treatment professional at "bed-side", so to speak). Alternatively, the embodiments also include microbeads intended to be used to achieve embolic effect only without application of a drug or therapeutic agent (e.g., "plain" or "bland" microbeads).

In some embodiments, the methods shown and described herein for loading a drug or therapeutic agent into microbeads may be applied to "bed-side" loading, as described in Example 12 and FIGS. 9A-9B.

Tumor treatment. In an important non-limiting example, the microbeads described herein may deliver drugs for treatment of vascularized tumors. For example, a number of drugs commonly used for oncology may be advantageously delivered by the microbead embodiments having a selected rate of biodegradation and drug release, wherein the inherent radiopacity of the bead copolymer aids in precise localized delivery to the tumor while minimizing systemic effects.

In some embodiments, the radiopaque, bioresorbable embolic microbeads described herein may provide a "multifaceted" treatment capability. For example, the microbeads may provide sustained, localized release of the drugs with two complementary therapeutic goals: one is sustained release of powerful chemotherapy drugs to shrink tumors; and a second is the sustained release of therapeutic agents designed to stimulate the immune system to attack tumors.

In one example of a multifaceted treatment method using an embodiment of the microbead described herein, a mixture of two or more distinct microbead types may be administered to a tumor site. In this example, a first type of microbead comprises one or more tumor-shrinking chemotherapy drug; and a second type of microbead comprises an immunotherapy agent. Each type of microbead may have a structure and composition suited to optimize the therapeutic effect of its constituent drug.

In another example of a multifaceted treatment method using the microbead embodiments, a single type of microbead comprises both of (i) more tumor-shrinking chemotherapy drug; and (ii) an immunotherapy agent. The structure and composition of the microbead embodiment is suited to permit effective delivery and elution timing of each therapeutic agent.

In some embodiments, controllable or tunable biodegradation of the microbeads described herein permit subsequent retreatment at a site of initial implantation, which may be highly advantageous in certain drug treatment strategies.

In another example of a multifaceted treatment method, use is made of the controllable bioresorbable properties of the microbeads described herein, so as to enable sequential retreatment at a tumor site for delivery of multiple therapeutic agents. For example, an initial embolic treatment of a tumor may include administration of a microbead described herein comprising a first drug or agent, the microbead structure and/or composition configured (in elution rate and/or biodegradation rate) to effectively delivery the first drug or agent. Retreatment may then be performed using a second microbead embodiment comprising a second drug or agent.

Likewise, embolization of a site, such as a tumor, may be controlled to create temporary ischemic conditions at the site without disruption of the vasculature. In some embodiments, the radiopaque bioresorbable microbeads described herein may comprise compositions which not only produce biodegradation products that are biocompatible, but also have been shown to be compatible with many drugs, such to avoid denaturing or rendering drugs ineffective.

Examples of Therapeutic Agents

Non-limiting examples of drugs or other therapeutic agents include:

A. Cisplatin—Commonly used for lung, ovary, carcinoma, breast, brain cancers, among other things. Cisplatin binds to DNA so as to prevent DNA replication, and cause apoptosis while increasing mitochondria oxidative stress. Cisplatin can be effective regardless of the target cell replication state.

B. Doxorubicin—Commonly used for breast, lung, gastric, ovarian, thyroid cancers, and myeloma, sarcoma, among other things. Doxorubicin disturbs TOPII Mediated DNA repair and generates free radicals to damage membranes, generally targeting replicating cells.

C. Cyclophosphamide—Used as anti-angiogenesis agent and often in conjunction with peptide cancer vaccines for immunotherapy, among other things. Cyclophosphamide targets cells regardless of replication state.

D. Paclitaxel—Used for breast, ovarian, prostate, gastric, non-small cell lung, head, neck cancers, among other things. Paclitaxel acts by locking tubulin structures in place, impairing mitosis.

E. Oxaliplatin—Used for colorectal and ovarian cancers, among other things, generally in conjunction with 5-Flourorcil. Oxaliplatin acts by crosslinking DNA and proteins.

F. 5-Flourorcil—Used for colorectal cancer and solid tumors, among other things, and may be used in conjunction with Leucovorin to improve efficacy. 5-Flourorcil acts by disrupting RNA synthesis.

G. Nivolumab/Pembrolizumab—IgG4 isotype antibodies that blocks a protective mechanism of cancer cells and allows the immune system to destroy those cancer cell. Used for melanoma and non-small cell lung cancer among other things.

H. Ipilimumab—A monoclonal antibody that works to activate the immune system by targeting CTLA-4, a protein receptor that downregulates the immune system. It is a cancer immunotherapy approved for use to treat melanoma.

I. Interleukin-2 (IL-2)—A biologic response modifier and cytokine to stimulate the immune system to attack cancer. Used in renal cell carcinoma and melanoma.

As one example, liver cancer, such as hepatocellular carcinoma, may typically present as a highly vascular solid tumor. Embolic microbead embodiments may be delivered to arterioles of the tumor so as to block blood supply, and to deliver a chemotherapeutic drug such as doxorubicin. In an embodiment, the microbeads may have a diameter in the range of about 100 microns to about 300 microns. The polymer material of the microbeads may be suited to degrade predictably, so as to release the drug content over a selected time period, for example about 2 to 6 months. An immunotherapy drug may also be administered via microbead embodiments described herein.

In some embodiments, the bioresorbable microbeads of the present disclosure have attributes that can enhance the effectiveness of certain drugs. For example, Paclitaxel and Doxorubicin may be advantageously used in low dosages over a prolonged period of time. Hydrophobic components of the copolymer embodiments described herein can interact with these drugs to act as a stable reservoir for prolonged elution at the microbead implantation site. Selectable biodegradation rate (e.g., by a mixture of carbonate and oxalyl ester bonds) can provide for such prolonged elution.

Carbonate Bonds

In certain embodiments, the copolymer material is synthesized by creation of carbonate bonds linking sub-units of either or both of the radiopaque and/or rubbery components. This may, for example, be accomplished by use of triphosgene (TP) as a polymerizing reactant, whereby the TP acts upon carbonyl and hydroxyl groups of respective monomers or oligomers in the reacting mixture. Typically, carbonate bonds in such a polymer chain are relatively stable to hydrolysis under physiological conditions. In certain embodiments, the copolymer comprises both PrD-di I2DAT and polyethylene glycol (PEG). EXAMPLE 1 below illustrates a general method of preparing such a copolymer. In this example, carbonate bonds are created using an excess of triphosgene (TP) as a reactant.

Oxalate Bonds

In certain embodiments, the copolymer material is synthesized by creation of oxalyl ester or oxalate bonds linking sub-units of either or both of the radiopaque and/or rubbery components. This may, for example, be accomplished by use of oxalyl chloride as a polymerizing reactant, whereby the oxalyl chloride acts upon carbonyl and hydroxyl groups of respective monomers or oligomers in the reacting mixture. Example 2 below describes a general method of preparing such a copolymer. In some instances, oxalate bonds in such a polymer chain are relatively vulnerable to hydrolysis.

Mixtures of Carbonate and Oxalate Bonds

In some embodiments, the polymerization scheme is configured to create a mixture of both carbonate bonds and oxalate bonds in the copolymer chain of the material forming the embolic microbeads. The particulars of the mixture, as described in detail below, permit the biodegradation characteristics of the microbeads to be tailored and matched to therapeutic requirements.

In some other embodiments, the copolymer likewise comprises both PrD-di I2DAT and polyethylene glycol (PEG). In these embodiments, both carbonate bonds (e.g., by addition of TP), and oxalate bonds (e.g., by addition of Oxalyl chloride) are formed, thereby achieving distinct properties of the resulting copolymer. Examples 3-5 below show several methods of preparations of such copolymers having both carbonate and oxalate bonds.

Particular Carbonate-Oxalate Synthesis Condensation Schemes and Bond-Arrangements In various microbead embodiments, synthesis of a polymer material may have one of several different timing schemes or strategies, in order to create a co-polymer material with varying arrangements and frequencies of carbonate and oxalate bonds. Both the frequency of each bond type (% of carbonate vs. % of oxalate), and the pattern or arrangement of carbonate and oxalate bonds along the copolymer change can affect the properties of the copolymer material.

FIG. 1 illustrates a generalized reaction scheme for condensation polymerization with triphosgene of two monomers A and B. For example, A may be PrD-di I2DAT and B may be PEG.

FIG. 2 illustrates the chemical structure of an exemplary generalized copolymer with mixture of carbonate and oxalate bonds.

As described in Examples 3-5 below, a condensation reaction is achieved in which stoichiometrically calculated portions of triphosgene (TP) and oxalyl chloride may be dissolved in appropriate solvents to provide respective reactant additives. Each of these reactant additives may then be added to a reaction mixture including desired precursor monomers or oligomers in a particular desired timing pattern:

(a) Simultaneous addition (e.g., Example 3)—the full portions of the triphosgene (TP) and oxalyl chloride reactant solutions are added to the reaction mixture at approximately the same time and the reaction of each with the precursor monomers or oligomers proceeds simultaneously. Simultaneous addition results in the formation of relatively even distribution of faster and slower hydrolysable chemical bonds along copolymer chains. This even distribution of highly hydrolysable chemical bonds leads to uniform degradation of microbeads.

(b) Sequential addition (e.g., Example 4)—one of the portions of the triphosgene (TP) and oxalyl chloride reactant solutions is selected to be are added to the reaction mixture first, and is allowed to react until the reaction is fully or approximately complete, followed by addition and reaction of the other portion. This consecutive or sequential manner of condensation results in the formation of blocks with highly hydrolysable chemical bonds, and blocks with slower hydrolysable chemical bonds along copolymer chains. The blockiness of resulting copolymer leads to at least two steps degradation of microbeads.

(c) Alternating addition (e.g., Example 5)—A variation of the sequential scheme in which each portion of the reaction solution is sub-divided into a desired number of sub-portions (e.g., 20 sub-portions), which sub-portions are then added in an alternating sequence, with an appropriate reaction time between additions, until all sub-portions have been added and reacted. This alternating sequence of the different coupling agents results in the formation of relatively small blocks of faster and slower hydrolysable chemical bonds along copolymer chains. The alternating distribution of small blocks of highly and slower hydrolysable chemical bonds has an effect on degradation kinetics of microbeads and can allow adjustment of degradation kinetics.

Following reaction, for example in (a)-(c) above, the copolymer material may be purified as described in the Examples, e.g., by precipitation from the reaction mixture (e.g., with IPA), followed by multiple dissolution (e.g., in DCM) and precipitation (IPA), followed in turn by drying.

Preparation of Micro-Beads

The purified copolymer material, e.g. as those described in Examples 1-6 may be formed into microbeads by various methods.

In one embodiment, microbeads may be prepared as described in Example 7. This includes dissolving the polymer material in a suitable solvent and adding the solution in a thin stream (e.g. from a syringe) to a receiving solution, in which beads are formed by disintegration of the stream.

Examples 9-13 also describe methods of making microbeads, and in particular making microbeads with a content of a drug or biologic agent. Other methods may be employed in preparing microbeads from the copolymer material, for example by Continuous Flow Beads (CFB) methods, to give uniform beads of desired size.

Porosity of Microbeads

Embodiments of microbeads described herein may have substantial porosity, which contributes to both compressibility and buoyancy, among other properties. Embodiments also includes a method of making spherical, radiopaque, biodegradable, compressible, resilient microparticles with interior and exterior porosity (exterior porosity refers to pores which open to the microbead surface).

Effects of Relative Proportions of Carbonate and Oxalate Bonds.

In embodiments, porosity of microbeads is created by formation of carbon dioxide gas which is formed during microbeads preparation due to degradation of previously incorporated easily hydrolysable or thermally instable chemical bonds (e.g. oxalate bonds).

In embodiments, during the formation of the microbeads (and/or during hydration of the microbeads) porosity may be created by means of decomposition of fast-degrading chemical bonds accompanied by release of volatiles such as carbon dioxide which form pores and/or "escape" channels. Porosity of microparticle could also be created by incorporation of porogen materials during beads formation stage and subsequent elimination them from already formed microbeads.

Methods of Microbead Drug Loading

Diffusion. As described herein, embodiments of microbeads described herein may be precipitated in a reaction in which carbon dioxide is produced, resulting in gas-filled pores. Depending on the reaction conditions, the pores may interconnect to create a sponge-like porosity.

Figure 3:
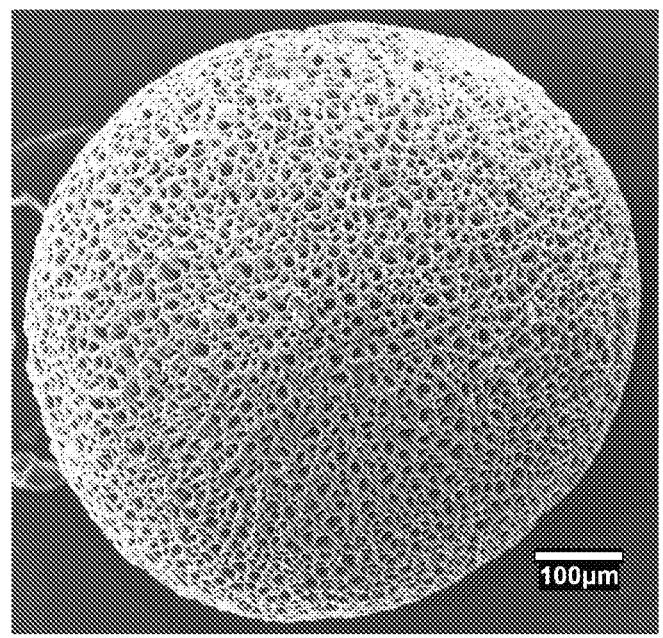
FIG. 3 illustrates a SEM image of high porosity radiopaque biodegradable microsphere made from copolymer 40% PrD-diI2DAT-co-40% PEG400-co-20% PCL1.25 k with ratio of carbonate to oxalate bonds of 75% to 25%.

As shown in FIG. 3, the surface of the generally spherical microbead contains a large portion of open pores, and thus allows pervasive communication with the bead interior. Thus, it may be seen that the pores provide a very substantial volume of voids within the bead, which voids can both act as a reservoir volume for drugs or biological agents, and also act to modulate the buoyancy and fluidic-deliverability characteristics of the microbeads.

Previously prepared dried microbeads may be loaded with drug content by diffusion (e.g., Example 12). A drug, mixture of drugs, and/or biological agent may be suspended in as suitable solvent and diffused into the microbead. FIGS. 9A-9B illustrate microbeads being charged with an example water soluble drug Doxorubicin (DOX). FIG. 9A illustrates a small cluster of native beads (before diffusion—light color). This may be contrasted with a similar cluster beads in FIG. 9B after diffusion of DOX into porous microbeads structure when beads are soaking in a drug solution. FIG. 9B is a close-up detail of the fully drug-loaded microbeads with intense orange color of DOX. In this particular non-limiting example the microbeads comprise a copolymer comprising 50% PrD-di I2DAT-co-30% PEG1 k-20% PCL1.25 k with ratio of carbonate/oxalate bonds=75%/25%.

Drug-loading by diffusion may be included as a step in manufacturing the microbeads as a medical product (pre-loaded), or alternatively, may be performed as part of the administration procedure, whereby a drug or agent is diffused into the beads under sterile conditions just prior to implant within the body (e.g. catheter delivery into a site within the vasculature). This latter method may be particularly suitable to certain biologic agents, such as perishable or sensitive agents.

In certain embodiments, diffusion of a drug in a solvent may be followed by evaporation of the solvent to form a deposition of the drug with the pores. This step may optionally be repeated to increase the drug content within the microbead.

Precipitation. In certain embodiments, a drug or agent may be stable and compatible in the solvent or mixture from which microbead embodiment is precipitated, the drug or agent being included within the body of the microbead. For example, copolymer microbeads embodiments have been prepared having Paclitaxel in solution as the microbeads are precipitated, the Paclitaxel then being present as crystals within the formed microbeads. The biodegradability then permits time-duration elution of the Paclitaxel at the site of implant.

FIG. 10 is a composite image which shows a microbead embodiment, which was made by precipitation of crystalline Paclitaxel as a mixture in a copolymer material. Example 9 describes an exemplary method for making such a microbead. Paclitaxel content exceeding 30% by weight has been demonstrated by these methods. It can be seen that crystalline drug showing through to the surface of the microbead, as particularly apparent in the enlarged portion of the image.

In Example 10, microbeads are prepared by encapsulating rapamycin (sirolimus) into the microbead in concentrations exceeding 25% by weight.

Figure 13:
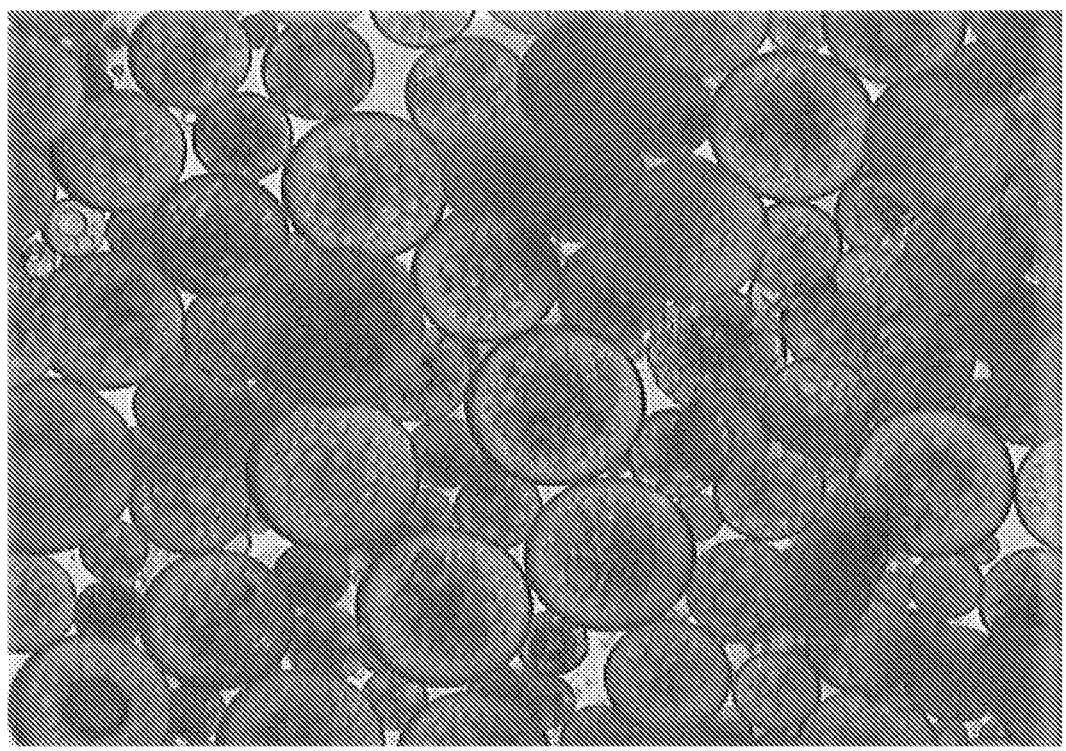
FIG. 13 illustrates DOX-loaded microbeads prepared from copolymer 50% PrDI2FD-co-50% PEG1 k with 100% carbonate bonds by encapsulation of DOX suspension in organic solvent.

In Example 13, microbeads are prepared by encapsulating Doxorubicin (DOX) from suspension of DOX in dichloromethane solution of embolic copolymers. Image of microparticles with encapsulated suspension of DOX is shown in FIG. 13. This method of allows to reach higher concentration of encapsulated drug DOX than diffusion method.

Encapsulation of Biological Agents in Radiopaque, Bioresorbable Microbeads

In Example 11, a biologic agent is encapsulated in a microbead embodiment, demonstrating the capability of microbead to deliver biologic agents to tumors and other anatomy. In this case the biologic is Bovine Serum Albumin (BSA), which is a suitable model for biotherapeutic and and/or large molecule agents. As described above, immunologic agents (e.g., nivolumab/pembrolizumab, ipilimumab, and Interleukin-2, and the like) are important in the treatment of tumors.

Microbeads Made from Latently Cross-Linkable Copolymer Materials

Figure 11:
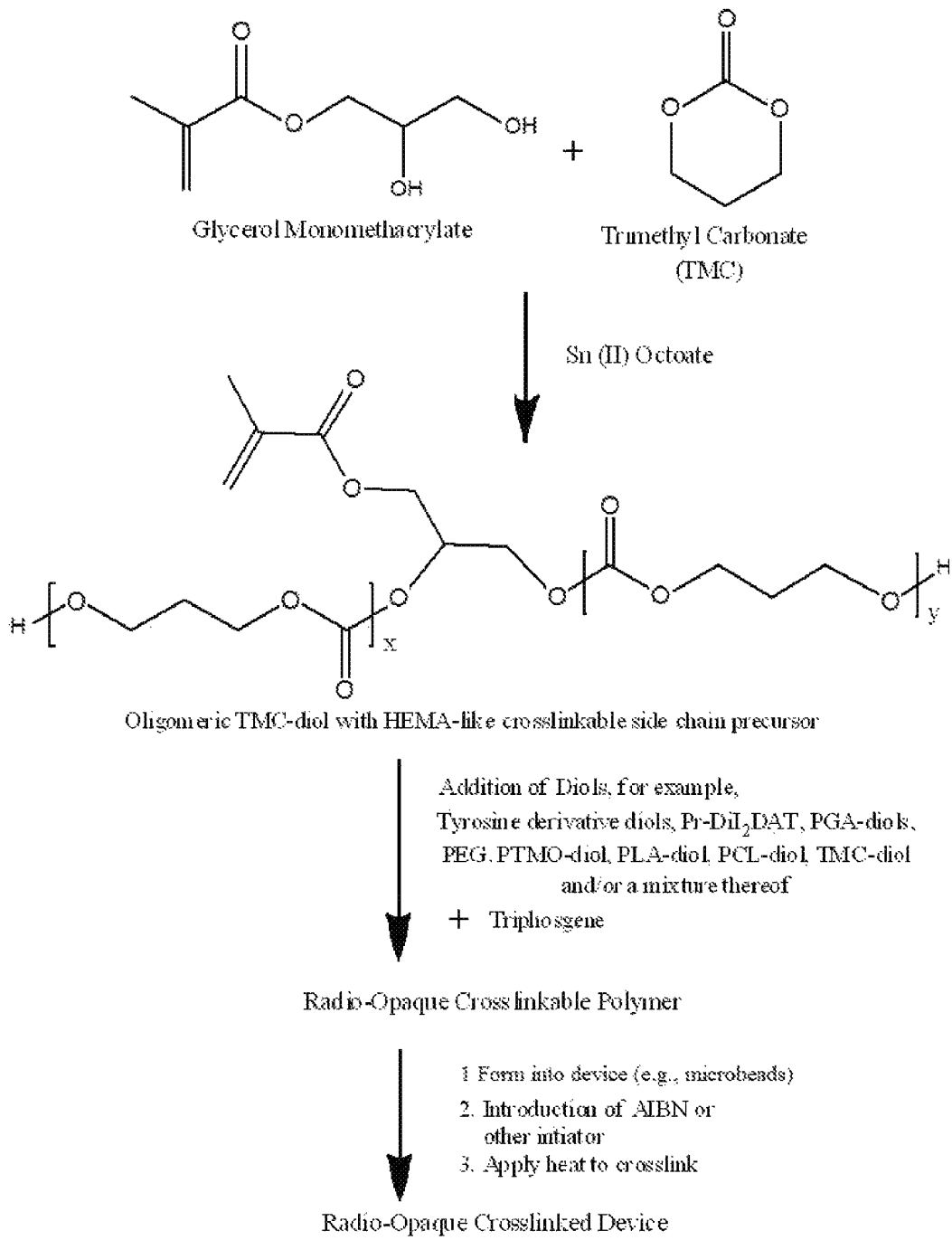
FIG. 11. shows a reaction scheme for making embodiments of microbeads comprising cross-linked polymer.

Embodiments of microbeads may alternatively comprise cross-linked copolymer materials. FIG. 11 shows a reaction scheme for making embodiments of microbeads comprising cross-linked polymer, whereby a co-polymer is prepared having pendant groups comprising HEMA or HEMA-like cross-linking groups which are latently cross-linkable. Following formation of pre-form microbeads, cross-linking is induced by application of a free-radical initiator.

Example 17 describes a method of treating the microbeads with a free radical initiator and conducting a subsequent free radical polymerization procedure to create biodegradable cross-linked microbeads. In this embodiment, (hydroxyethyl) methacrylate or HEMA is incorporated in a polymer composition. Subsequently a free radical initiator is added to a solution of polymer at the bead-forming stage, so that the initiator diffuses into beads, and gets incorporated into bead. Heat may be applied to initiate polymer cross-linking.

Microbeads Comprising Copolymer Blends

Microbeads also could be produced from a mixture (or blend) of copolymers, comprised purely by Carbonate and Oxalate bonds. In the case of blends of copolymers, degradation will be two steps process. The copolymer with Oxalate bonds will degrade first, this will alter the physical structure of microbeads and promote the degradation of copolymer with Carbonate bonds at the later stages. The rate of hydrolytic degradation of microbeads and duration of each degradation step could be adjusted by incorporation of different ratios of copolymers with Oxalyl bonds and Carbonate bonds. See Example 8 below.

Figure 12A:
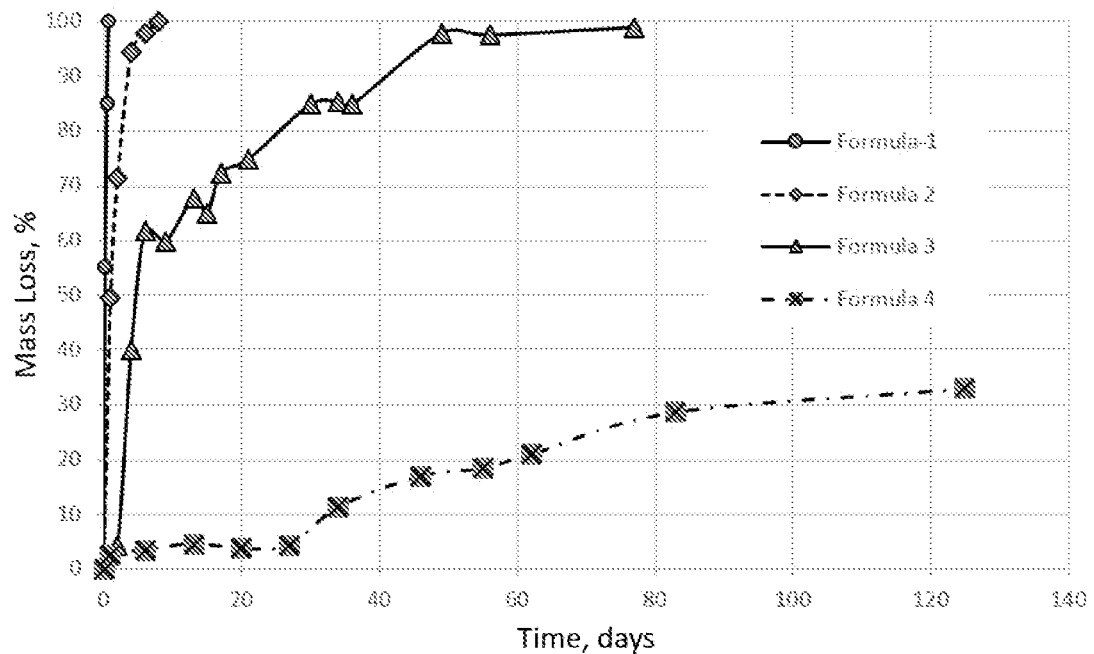
FIGS. 12A and 12B illustrate the biodegradation patterns of a number of particular non-limiting example formulas of microspheres comprising copolymers and blends of copolymers, achieving multi-phase drug elution patterns.
Figure 12B:
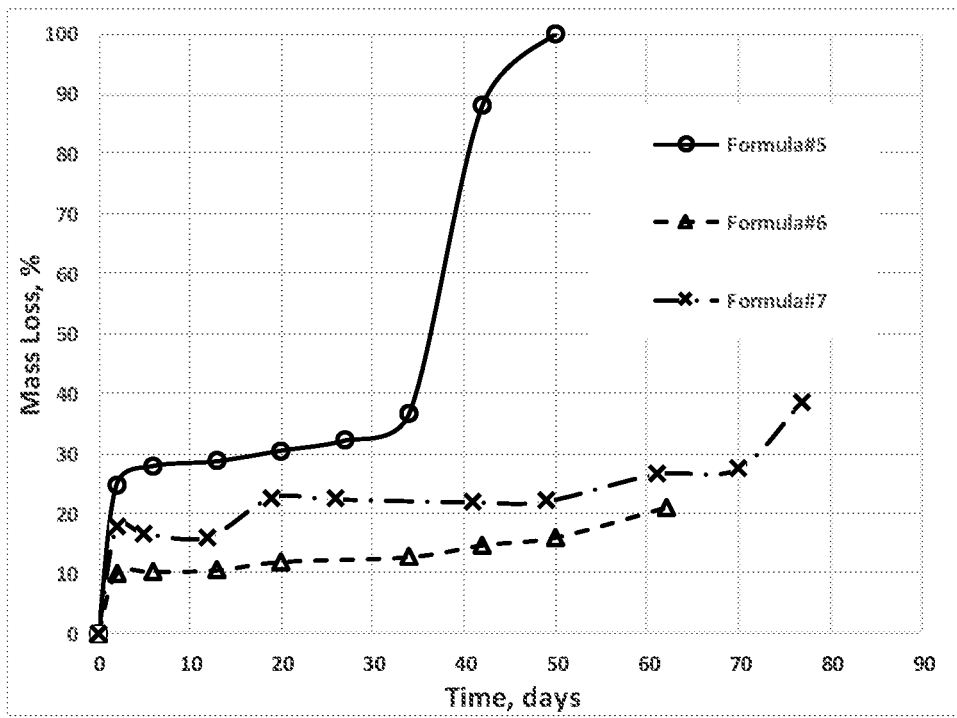

The illustrative examples of achievable degradation profile are presented on FIGS. 12A and 12B.

FIG. 12A demonstrates the degradation kinetic (mass loss) of copolymer prepared with 100% carbonate bonds (Formula #4—slow degradation), copolymer with 100% oxalate bonds (Formula #1—fast degradation in 1-24 hours) and copolymers with mixture of carbonate and oxalate bonds (Formulas #2 and 3—intermediate degradation).

In this particular non-limiting example, instant Formulas 1~4 comprise:

Formula #1: Copolymer 70% PrD-di I2DAT-co-30% PEG1 k with 100% oxalate bonds.

Formula #2: Copolymer 40% PrD-di I2DAT-co-30% PEG400-co-30% PCL1.25 k with 80% carbonate and 20% oxalate bonds.

Formula #3: Copolymer 40% PrD-di I2DAT-co-30% PEG1 k-co-30% PCL1.25 k with 80% carbonate and 20% oxalate bonds.

Formula #4: Copolymer 50% PrD-di I2DAT-co-50% PEG1K with 100% carbonate bonds.

FIG. 12B demonstrates the degradation kinetics (mass loss) of microbeads prepared from blends of copolymer comprised by purely carbonate or oxalate chemical bonds.

For example, Formulas #5-7 prepared as blends of copolymers comprised purely by carbonate or oxalate bonds. Ratios of copolymers by weight are 50%/50% (Formula #5), 70%/30% (Formula #7) and 90%/10% (Formula #6).

In this particular non-limiting example, the Formulas 5-7 comprise:

Formula #5: Blend of Copolymer 50% PrD-di I2DAT-co-50% PEG1K with 100% carbonate bonds and Copolymer 50% PrD-di I2DAT-co-50% PEG1 k with 100% oxalate bonds, 50/50% w/w.

Formula #6: Blend of Copolymer 50% PrD-di I2DAT-co-50% PEG1K with 100% carbonate bonds and Copolymer 50% PrD-di I2DAT-co-50% PEG1 k with 100% oxalate bonds, 90/10% w/w.

Formula #7: Blend of Copolymer 50% PrD-di I2DAT-co-50% PEG1K with 100% carbonate bonds and Poly(50% PrD-di I2DAT-co-50% PEG1 k with 100% oxalate), 70/30% w/w.

Adjusting ratio of iodinated structural component (PrD-diI2DAT) and rubbery component (PEG400 or PEG1000), ratio of Carbonate to Oxalate bonds in single copolymer or utilizing blends of copolymers, a wide spectrum of degradation profiles could be achieved, including multi-step degradation. For example, Formula 5 shows a well-defined plateau after a prompt mass-loss of about 30%, followed by a second phase of mass-loss beginning at about 20 days. Formula 7 (lower oxalate %) shows a similar well-defined plateau after prompt mass-loss of about 20%, followed by a later second phase of mass-loss beginning at about 70 days.

This property is useful, not only for achieving of desirable embolization effect, but also for administration of drug or other therapeutic or biologically active agents when they are incorporated into microbeads. Thus the embodiments of blends of copolymers as exemplified herein permit configurations of embolic microspheres or microbeads which elute one or more therapeutic agents or drugs in a multi-phase time release program.

EXAMPLES

Examples 1 through 6 demonstrate the alternative schemes for using Triphosgene (TP) and Oxalyl chloride to form a mixture of carbonate and oxalyl linking bonds between monomer/macromers to form a copolymer material. The exemplary non-limiting embodiments are copolymers of PrD-di I2DAT and Polyethylene glycol (PEG).

The term "PrD-di I2DAT", as used herein, is an abbreviation referring to the di-ester of 1, 3-propanediol ("PrD") with di-iodinated-desaminotyrosine ("I2DAT).

Example 1—Poly (50% PrD-Di I2DAT-Co-50% PEG1K Carbonate). Polymer Preparation for Embolotherapy Using Triphosgene Only To a 3 L flask were added 75 g of each, Polyethylene glycol (PEG, Mn~1000 Da) and PrD-di I2DAT. 1200 g of Dichloromethane (DCM) and 54.8 g of Pyridine were added to the flask. The mixture was stirred until the solution becomes clear.

In a 250 ml bottle, 19 g Triphosgene (TP) was dissolved in 76 g of DCM. The amount of TP is at least 1.2 to 1.3 times molar equivalent of the OH groups. With stirring of the solution in the flask, the TP solution was introduced into the flask at a slow rate so that the addition time was about 1.5 hrs. At this point the reaction mixture is viscous. More TP may be added depending on the molecular weight desired.

The polymer was isolated by precipitation using 2-propanol (IPA) and followed by multiple IPA washings. The crude polymer was re-dissolved in DCM followed by precipitation and washes in IPA. This was repeated until the polymer was free of pyridine. The polymer was then placed in a vacuum oven under dynamic vacuum until dry.

Example 2—Poly (50% PrD-Di I2DAT-Co-50% PEG1K Oxalate). Polymer Preparation for Embolotherapy Using Oxalyl Chloride Only To a 3 L flask were added 75 g of each, Polyethylene glycol (PEG, Mn~1000 Da) and PrD-di I2DAT. 1200 g of Dichloromethane (DCM) and 54.8 g of Pyridine were added to the flask. The mixture was stirred until the solution becomes clear.

In a 250 ml bottle, 25 g Oxalyl Chloride (OC) was dissolved in 100 g of DCM. The amount of OC is at least 1.2 to 1.3 times molar equivalent of the OH groups. With stirring of the solution in the flask, the OC solution was introduced into the flask at a slow rate so that the initial addition time was about 1.5 hrs. At this point the reaction mixture is viscous. More OC may be added depending on the molecular weight desired.

The polymer was isolated by precipitation using 2-propanol (IPA) and followed by multiple IPA washings. The crude polymer was re-dissolved in DCM followed by precipitation and washes in IPA. This was repeated until the polymer was free of pyridine. The polymer was then placed in a vacuum oven under dynamic vacuum until dry.

Example 3—Simultaneous Addition. Preparation of Polymer with Both Oxalate and Carbonate Linking Groups An appropriate mixture of PrD-di I2DAT and Polyethylene glycol of desirable molecular weight were dissolved in DCM in a 4-necked flask equipped with an overhead stirrer, a nitrogen inlet and two ports for liquid addition. Pyridine equivalent to 3 to 4 times the OH group in the mixture was added. About ½ equivalent of triphosgene of the total number of OH groups was dissolved in DCM. Oxalyl chloride equivalent to ½ the total OH groups was dissolved in similar amount of DCM used to dissolve TP.

With moderate stirring both TP and Oxalyl chloride solutions were added at the same rate. After the addition was complete the reaction mixture was stirred for 30 min and the polymer was isolated by precipitation with IPA. The polymer was further purified by multiple dissolution (DCM) and precipitation (IPA) until all the by-products were removed. The polymer was dried in vacuum oven at 40° C.

Example 4—Sequential Addition. Preparation of Polymer with Both Oxalate and Carbonate Linking Groups An appropriate mixture of PrD-di I2DAT and Polyethylene glycol of desirable molecular weight were dissolved in DCM in a 4-necked flask equipped with an overhead stirrer, a nitrogen inlet and two ports for liquid addition. Pyridine equivalent to 3 to 4 times the OH group in the mixture was added. About ½ equivalent of the total number of OH groups was dissolved in DCM. Oxallyl chloride equivalent to ½ the total OH groups was dissolved in similar amount of DCM used to dissolve TP.

With moderate stirring oxalyl chloride solutions was added to the flask. After the addition was complete the reaction mixture was stirred for 10 min and then the TP solution was added at the same rate. After the addition was complete the polymer was isolated by precipitation with IPA. The polymer was further purified by multiple dissolution (DCM) and precipitation (IPA) until all the by-products were removed. The polymer was dried in vacuum oven at 40° C.

Example 5—Alternate Addition. Preparation of Polymer with Both Oxalate and Carbonate Linking Groups An appropriate mixture of PrD-di I2DAT and Polyethylene glycol of desirable molecular weight were dissolved in DCM in a 4-necked flask equipped with an overhead stirrer, a nitrogen inlet and two ports for liquid addition. Pyridine equivalent to 3 to 4 times the OH group in the mixture was added. Triphosgene (about ½ equivalent of the total number of OH) groups was dissolved in DCM. Oxallyl chloride equivalent to ½ the total OH groups was dissolved in similar amount of DCM used to dissolve TP.

With moderate stirring approximately 1/20th of oxalyl chloride solutions was added to the flask. Addition was stopped and after stirring for 5 min approximately 1/20th of TP solution was added. The addition sequence was repeated until both reagents were completely added. After the addition was complete the reaction mixture was stirred for 30 min and the polymer was isolated by precipitation with IPA.

The polymer was further purified by multiple dissolution (DCM) and precipitation (IPA).

Example 6 Preparation of Poly(40% PrD-Di I2DAT-Co-30% PEG1 k-Co-30% PCL1.25 k with 80% Carbonate-20% Oxalate Linking Groups Example 6 demonstrates an exemplary method for making alternative copolymer material suitable for preparation of generally spherical microbeads described herein.

To a dried 3 L jacketed vessel set at 35° C., a mixture of PrD-di I2DAT (60 g, 0.0685 mols), Polyethylene Glycol 1000 g/mol (45 g, 0.0450 mols), and Polycaprolactone 1250 g/mol (45 g, 0.0360 mols) were added. Vessel assembly was completed with a 4-necked lid and equipped with a stirring blade assembly and motor. The mixture was stirred overnight under N2. After stirring overnight, 1200 g of dichloromethane (DCM) was added to the flask followed by 50.99 g of pyridine and the mixture was allowed to dissolve.

In a separate container, a 20% ($W_{Triphosgene}/W_{Solution}$) solution of Triphosgene was made by adding 13.6 g (0.1196 mols) and 54.42 g of DCM.

In another separate container, a 20% ($W_{Oxalyl\ Chloride}/W_{Solution}$) solution of Oxalyl Chloride was made by adding 4.36 g (0.0299 mols) and 17.46 g of DCM.

The two solutions were added to the 3 L jacketed vessel containing the monomer mixture via pumps over a period of 3 hours in an alternating fashion until the desired viscosity has been reached. After the reaching the final viscosity, the reaction was stopped by adding a 125 ml of a 10% water in tetrahydrofuran solution. The polymer was purified by a series of precipitation and washes with isopropanol (IPA) and multiple dissolutions in DCM. The isolated polymer was oven dried at 45° C. under vacuum.

Examples 7 through 17 demonstrate exemplary methods for making spherical microbeads described herein. Example 7 describes one exemplary embodiment of a method of making spherical microbeads. Example 8 demonstrates an exemplary procedure for preparation of microbeads from blend of copolymer materials. Examples 9-13 demonstrate methods and procedures for incorporating or otherwise including one or more drugs, therapeutic agents and/or biological agent into embodiments of microbeads described herein. Examples 14-17 describe microbeads comprising cross-linked polymer materials, demonstrating step-wise the preparation of various related pre-cursors and methods of such microbead preparation. In Examples 7 and 8, copolymer material compositions may be employed comprising oxalate linkage bonds, and that, in such case, the methods described may produce microbeads having a porous structure.

Example 7—Preparation of Beads

Microbeads of Examples 1-6 were prepared by introducing solution of polymer in methylene chloride (e.g., in the range 5-25%) into stirring 0.5% solution (e.g., in the range of about 0.5 to 2.5%) of poly(vinyl alcohol) ("PVA"), formation of microbeads suspension in PVA, washing microbeads with water, coating with mannitol solution and lyophilization of microbeads.

Prepare a 0.5% solution of PVA by dissolving 4 g of "cold water soluble PVA" in 800 mL of DI water overnight. 5 g of the embolic polymer was dissolved in 50 mL of methylene chloride in a glass bottle by stirring using magnetic stirrer or other means. 600 mL of PVA solution was placed in 2 L glass beaker and stirred at 700 rpm using an overhead stirrer. The polymer solution was introduced in one continuous stream to the stirred PVA solution using a 60 mL syringe and a 16-gauge needle. The suspension was allowed to stir for 1 h-24 h under a fume hood and then the stirring was stopped.

The supernatant was decanted and discarded. The beads were washed 5 times with 100 mL of a 2% solution of mannitol by mixing for approximately 30 to 60 seconds the beads after each addition of wash solution. The wet beads were transferred to a 100 mL flask along with 25 mL mannitol solution. The beads along with mannitol solution were frozen using dry ice/IPA or liquid nitrogen while rotating the flask to coat the frozen material onto the walls. The contents of the flask were lyophilized until all the ice sublimes. The dried beads along with mannitol were placed on top of the sieve set consisting of 500, 300, 180, and 90 micron sieves with a receiving pan at the bottom. This divides the beads into the following ranges: >500, 300-500, 180-300, and <90 microns. Beads were then packaged under Nitrogen and stored.

There are other methods of making beads e.g. Continuous Flow Beads (CFB). This method is reported to give uniform beads of desired size.

Example 8—Preparation of Microbeads from Blend of Poly (50% PrD-Di I2DAT-Co-50% PEG1K 100% Carbonate and Poly(50% PrD-Di I2DAT-Co-50% PEG1K 100% Oxalate, 60/40% w.w Prepare a 0.5% solution of PVA by dissolving 10 g of "cold water soluble PVA" in 2000 mL of DI water overnight. 3 g of Poly (50% PrD-di I2DAT-co-50% PEG1K 100% carbonate) and 2 g of Poly (50% PrD-di I2DAT-co-50% PEG1K 100% oxalate) was dissolved in 50 mL of DCM in a glass bottle by stirring using magnetic stirrer or other means.

700 mL of PVA solution was placed in 2 L glass beaker and stirred at 320 rpm using an overhead stirrer. Five 10 ml syringes were filled with polymer solution. A 1/16" tube was affixed to a 21.5 Ga needle. The 21.5 Ga needle was positioned above the surface of the PVA solution. Using a syringe pump, the contents of each syringe was introduced to the PVA solution at a rate of 1 ml/min via the tube/needle. The suspension was stirred for at least 2 hrs.

The supernatant was decanted and discarded. The beads were washed with 100 mL of a DI water and then decanted for a total of 3 water washes. The beads were then washed with 100 ml of a 1.25% aqueous mannitol solution and decanted for a total of 2 mannitol washes. The wet beads were transferred to a 250 mL flask along with at least 100 mL of mannitol solution. The mannitol solution was decanted and replaced by 50 ml of mannitol solution. The beads along with mannitol solution were frozen using dry ice/IPA while being rotated.

The frozen contents of the flask were lyophilized until all the ice sublimes. The dried beads along with mannitol were placed on top the sieve set separating them into appropriate size ranges and then packaged.

Example 9—Preparation of Encapsulated Paclitaxel into Microbeads

The following solutions were prepared for the manufacturing of the embolic beads.

Polymer Solution with Paclitaxel—In a 250 ml vial, 35 ml of DCM was added to 5.95 g of Example 1 and 1.05 g of Paclitaxel (15% $W_{Paclitaxel}/W_{Total\ Solids}$) to make a 20% $W_{Total\ Solids}/V_{DCM}$ solution. The solution was mixed by inversion overnight to dissolve using a Roto-Shake Genie.

PVA Solution—In a 1 L beaker, 4 g of poly vinyl alcohol (PVA, MW 30000-70000 g/mol) was added to 800 ml of water to make a 0.5% $W_{PVA}/V_{Water}$ solution. The solution was stirred with a magnetic stirrer, mixing overnight to dissolve.

Mannitol Solution—In a 1 L Erlenmeyer flask, 7.5 g of Mannitol was added to 600 ml of water to make a 1.25% $W_{Mannitol}/V_{Water}$ solution. The solution was stirred with a magnetic stirrer until dissolved. The solution was made prior to the final wash stages to the microbeads.

The manufacturing of microbeads was as follows. The PVA solution was strained through a Texwipe directly into a 1 L cylindrical reaction vessel removing gross particulate. It was stirred at 325 rpm. The polymer solution with Paclitaxel was added to a several 10 ml syringes. The solution was added to the PVA solution, just above the surface. The mixture was stirred for 3 hours. After stirring, the beads were allowed to settle, and the aqueous phase was decanted out of the vessel. The beads were washed three times with 50 ml of water followed by three washes with 50 ml of mannitol solution. The beads were then frozen in 20 ml of mannitol solution using a dry ice/IPA bath. The frozen beads were placed in an oven and dried under high vacuum. After drying the beads were separated through a series of sieves with appropriate mesh sizes.

Example 10—Preparation of Encapsulated Rapamycin into Microbeads

The following solutions were prepared for the manufacturing of the embolic beads.

Polymer Solution with Rapamycin—In a 250 ml vial, 35 ml of DCM was added to 5.25 g of Example 1 and 1.75 g of Rapamycin (25% $W_{Rapamycin}/W_{Total\ Solids}$) to make a 20% $W_{Total\ Solids}/V_{DCM}$ solution. The solution was mixed by inversion overnight to dissolve using a Roto-Shake Genie.

PVA Solution—In a 1 L beaker, 4 g of poly vinyl alcohol (PVA, MW 30000-70000 g/mol) was added to 800 ml of water to make a 0.5% $W_{PVA}/V_{Water}$ solution. The solution was stirred with a magnetic stirrer, mixing overnight to dissolve.

Mannitol Solution—In a 1 L Erlenmeyer flask, 7.5 g of Mannitol was added to 600 ml of water to make a 1.25% $W_{Mannitol}/V_{Water}$ solution. The solution was stirred with a magnetic stirrer until dissolved. The solution was made prior to the final wash stages to the microbeads.

The manufacturing of microbeads was as follows. The PVA solution was strained through a texwipe directly into a 1 L cylindrical reaction vessel removing gross particulate. It was stirred at 325 rpm. The polymer solution with Rapamycin was added to a several 10 ml syringes. The solution was added to the PVA solution, just above the surface. The mixture was stirred for 3 hours. After stirring, the beads were allowed to settle, and the aqueous phase was decanted out of the vessel. The beads were washed three times with 50 ml of water followed by three washes with 50 ml of mannitol solution. The beads were then frozen in 20 ml of mannitol solution using a dry ice/IPA bath. The frozen beads were placed in an oven and dried under high vacuum. After drying the beads were separated through a series of sieves with appropriate mesh sizes and packaged.

Example 11—Preparation of Bovine Serum Albumin (BSA) into Microbeads

The following solutions were prepared for the manufacturing of the embolic beads.

Polymer Solution with BSA—In a 250 ml vial, 35 ml of DCM was added to 7.5 g of Example 1 to make a 20% $W_{Polymer}/V_{DCM}$ solution. The solution was mixed by inversion overnight to dissolve using a Roto-Shake Genie. To the dissolved polymer solution was added 1 g of BSA and the solution was mixed thoroughly.

PVA Solution—In a 1 L beaker, 16 g of poly vinyl alcohol (PVA, MW 30000-70000 g/mol) was added to 800 ml of water to make a 2.0% $W_{PVA}/V_{Water}$ solution. The solution was stirred with a magnetic stirrer, mixing overnight to dissolve.

Mannitol Solution—In a 1 L Erlenmeyer flask, 7.5 g of Mannitol was added to 600 ml of water to make a 1.25% $W_{Mannitol}/V_{Water}$ solution. The solution was stirred with a magnetic stirrer until dissolved. The solution was made prior to the final wash stages to the microbeads.

The manufacturing of microbeads was as follows. The PVA solution was strained through a Texwipe directly into a 1 L cylindrical reaction vessel removing gross particulate. It was stirred at 325 rpm. The polymer solution with BSA was added to a several 10 ml syringes. The solution was added to the PVA solution, just above the surface. The mixture was stirred for 3 hours. After stirring, the beads were allowed to settle, and the aqueous phase was decanted out of the vessel. The beads were washed three times with 50 ml of water followed by three washes with 50 ml of mannitol solution. The beads were then frozen in 20 ml of mannitol solution using a dry ice/IPA bath. The frozen beads were placed in an oven and dried under high vacuum. After drying the beads were separated through a series of sieves with appropriate mesh sizes and packaged.

Example 12—Diffusion of Doxorubicin into Microbeads

The following solutions/materials were prepared for the drug loading of the embolic beads.

Doxorubicin Solution in Water—In a 200 ml amber bottle, 100 ml of HPLC grade water was added to 200 mg of Doxorubicin to make a 0.2% $W_{Doxorubicin}/V_{water}$ solution. The solution was mixed by vortexing for 1 minute, 2 minutes of sonication, and then mixed by inversion overnight to dissolve using a Roto-Shake Genie. A portion of this solution can be analyzed for drug content by HPLC.

Previously prepared dried microbeads—Drug loading successfully performed with varying bead size, different copolymer compositions based on PrD-di I2DAT and PEG, as well as with varying copolymer blends.

The diffusion of Doxorubicin into microbeads was as follows. Approximately 50 mg of dried microbeads were added to a 4 mL screw-top glass vial. Add 3 mL of the 0.2% Doxorubicin solution to the microbeads. The sample was mixed by inversion for 1 to 23 hours using the Roto-Shake Genie. After mixing, the beads were allowed to settle, and the supernatant was decanted. The drug-loaded beads were then ready for immediate use or analysis. FIG. 9 illustrates incorporation of DOX by diffusion method.

Example 13—Encapsulation of Doxorubicin into Microbeads from DOX Suspension in Organic Solvent Prepare a suspension of 25 mg of doxorubicin in 10 mL of a 5% w/v embolic polymer in dichloromethane solution. Fully mix the suspension by agitation, and deliver by 21 ½ gauge needle into a stirring vessel of 0.5% poly(vinyl alcohol). Microbeads will form, encapsulating the suspended Doxorubicin particles. Decant from poly(vinyl alcohol) solution. See FIG. 13 for image. This method can lead to higher Doxorubicin loading than diffusion methods.

Examples 14 through 17 below describe aspects of making embodiments of microbeads comprising cross-linked polymer, whereby a co-polymer was prepared having pendant groups comprising HEMA or HEMA-like cross-linking groups which were latently cross-linkable. Following formation of pre-form microbeads, cross-linking was induced by application of a free-radical initiator.

Example 14—Preparation of HEMA Containing Diol (Compound I)

In a 1 liter round-bottomed flask were placed Glyceryl monomethacrylate (100 g, 0.624 mols), trimethylene carbonate (318 g, 3.12 mol to 636 g, 6.24 mol) and heated under nitrogen atmosphere till all the solids melt. The flask was then heated at 130° C. and Sn(II)octoate (0.24 g, 500 ppm) was added to the flask. The flask was heated at this temperature for 4 h. The flask was then allowed to cool to room temperature. To remove unreacted monomers and catalyst the product was dissolved in dichloromethane (DCM) and precipitated with heptane twice. The product was dried in a vacuum oven at 30° C. for 24 h. Purity of the product was determined by 1H NMR. The product was used without further treatment. In the place of TMC, other compounds such as Lactide (L or D,L), caprolactone, glycolide etc. can be used.

Example 15—Preparation of the Pre-Polymer with HEMA

Reaction of compound I with PrD-di I2DAT or other diol monomers or polymers.

In a 1 Liter round-bottomed flask was placed 100 g of compound I. To the flask were also added PrD-di I2DAT, polylactic acid diol (or oligocaprolactone, or oligoTMC or oligoglycolide) or mixtures of these to get desired copolymer. About 3 times excess pyridine was also added. Triphosgene (slightly more than ⅓ of the OH group) was dissolved in chloroform. With moderate stirring, triphosgene solution was introduced into the reaction flask at slow rate until the viscosity of the reaction mixture reaches desired value. The product was isolated by precipitation from 2-propanol or other suitable solvents. The precipitate was purified by re-dissolving in DCM and re-precipitation in IPA several times until all by-products of the reaction were removed. The product was dried in vacuum oven at a suitable temperature.

Example 16—Preparation of Microbeads Containing HEMA

Microbeads may also be prepared from the copolymer material from Example 15, using the method described in Example 7.

Example 17—Introduction of Free Radical Initiator into the Microbeads

To introduce free radical initiator into the microbeads, e.g. the microbeads produced in Example 16, a suitable solvent or mixture of solvents is found. The solvent should dissolve the free radical initiator. It should not dissolve the prepolymer; but should swell the polymer slightly so that some initiator gets absorbed into the device. A solution of initiator such as AIBN was prepared in this solvent mixture (a 1:1 mixture of acetone and heptane works in most cases). The dry microbeads were added to the AIBN solution for known length of time and then taken out and treated appropriately to obtain beads that do not stick together. The microbeads were cross linked by suitable triggering of latently cross-linkable pendant groups on copolymer.

What is claimed is:

1. Embolic spherical microparticles, comprising:
    a copolymer material having at least one radiopaque iodine-containing component and at least one rubbery component;
    wherein the rubbery component comprises oligomers or macromers of PEG (polyethylene glycol), PCL (polycaprolactone), PTMO poly(tetramethylene oxide), PTMC poly(trimethylene carbonate) or combinations thereof, and the rubbery component has a Tg below about 37° C.;
    wherein the radiopaque iodine-containing component comprises iodinated phenyl-containing monomers, oligomers, or macromers,
    wherein the at least one radiopaque iodine-containing component and the at least one rubbery component are connected by two or more different types of chemical bonds comprising fast degrading and slow degrading chemical bonds with different affinities to hydrolysis such that the different chemical bonds have different rates of in vivo hydrolytic degradation, and one type of chemical bonds is oxalate bond, and
    wherein the microparticles have internal and/or external porosity formed by the decomposition of fast degrading oxalate bonds.

2. The embolic spherical microparticles of claim 1, wherein the rate of hydrolytic degradation of the copolymer material is controlled by the relative amount of fast and slow degrading chemical bonds.

3. The embolic spherical microparticles of claim 2, wherein the ratio of fast to slow degrading chemical bonds is in the range from about 100:1 to about 1:100.

4. The embolic spherical microparticles of claim 1, wherein the ratio of the at least one radiopaque iodine-containing component to the at least one rubbery component is from about 10:1 to about 1:10.

5. The embolic spherical microparticles of claim 1, wherein the copolymer comprises more than one rubbery components with different hydrophilicity and different affinity to swelling in water or biologically relevant liquid media, and wherein the ratio between two different rubbery components with different hydrophilicity/swelling ability is in the range from about 100:1 to about 1:100.

6. The embolic spherical microparticles of claim 1, wherein hydration of the microparticles to about 80%-90% of a fully hydrated state occurs in 1 to 3 minutes following contact with a liquid aqueous media.

7. The embolic spherical microparticles of claim 1, wherein the internal/external porosity is formed by the release of volatile(s) resulting from the decomposition of the fast degrading oxalate bonds.

8. The embolic spherical microparticles of claim 7, wherein the volatile comprises carbon dioxide.

9. The embolic spherical microparticles of claim 1, wherein the porosity is further created by incorporation of porogen materials during microparticle formation and subsequent elimination of the porogens from the formed microparticles.

10. The embolic spherical microparticles of claim 1, wherein the at least one radiopaque iodine-containing component comprises monomers, oligomers or macromers of one or more of I2DTE (di-iodinated desaminotyrosyl tyrosine ethyl ester), I2DAT (di-iodinated desaminotyrosine), PrD-di I2DAT (di-ester of 1,3-propanediol with I2DAT), or combinations thereof.

11. The embolic spherical microparticles of claim 1, wherein the at least one radiopaque iodine-containing component comprises a repeating unit having the structure:

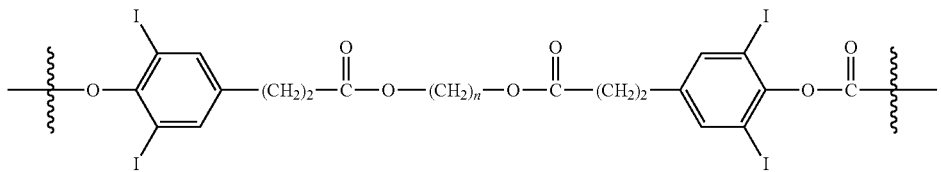

wherein n is an integer from 1 to 18.

12. The embolic spherical microparticles of claim 1, wherein the microparticles comprise a blend of at least two different constituent copolymers, each of the constituent copolymers comprises a main polymer chain having an amount of carbonate bonds and an amount of oxalate bonds; and
wherein the two constituent copolymers differ substantially in the amount of oxalate bonds relative to the amount of carbonate bonds such that one of the two constituent copolymers hydrolytically degrades in vivo at a higher rate than the other constituent copolymer, resulting in a multiple step or phased degradation of the microparticles.

13. The embolic spherical microparticles of claim 1, wherein the microparticles further comprise one or more therapeutic agents.

14. An embolization suspension, comprising a solution, and embolic spherical microparticles of claim 1 suspended in the solution, wherein the microparticles are hydrated and have diameters between about 40 μm to about 2000 μm.

15. The embolization suspension of claim 14, wherein the suspension comprises a contrast medium and a saline solution in the ratio from about 10:90 to about 90:10.

16. The embolic spherical microparticles of claim 1, wherein the microparticles are radiopaque and biodegradable.

17. The embolic spherical microparticles of claim 1, wherein the two or more different types of chemical bonds comprise carbonate bond and oxalate bond.

* * * * *